(12) United States Patent
Aberbach et al.

(10) Patent No.: US 11,793,496 B2
(45) Date of Patent: Oct. 24, 2023

(54) MEANS FOR COLLECTING SAMPLES OF URINE, DATA AND METHODS THEREOF

(71) Applicants: Varda Aberbach, Tel Aviv (IL); Daniel Shahaf, M.P. Emek Ha-Yarden (IL)

(72) Inventors: Varda Aberbach, Tel Aviv (IL); Daniel Shahaf, M.P. Emek Ha-Yarden (IL)

(*) Notice: Subject to any disclaimer, the term of this patent is extended or adjusted under 35 U.S.C. 154(b) by 90 days.

(21) Appl. No.: 17/124,892

(22) Filed: Dec. 17, 2020

(65) Prior Publication Data
US 2021/0128119 A1 May 6, 2021

Related U.S. Application Data

(63) Continuation-in-part of application No. 16/904,665, filed on Jun. 18, 2020.

(60) Provisional application No. 62/863,289, filed on Jun. 19, 2019.

(51) Int. Cl.
*A61B 10/00* (2006.01)

(52) U.S. Cl.
CPC .................. *A61B 10/007* (2013.01)

(58) Field of Classification Search
CPC .............. A61B 10/007; A61B 10/0096; G01N 1/2035; G01N 2001/2085; G01N 1/20; G01N 2001/2078
USPC .... 600/573, 574; 73/863.41, 863.51–863.53, 73/864.51, 864.52; 436/164
See application file for complete search history.

(56) References Cited

U.S. PATENT DOCUMENTS

| | | | | |
|---|---|---|---|---|
| 4,557,274 A | * | 12/1985 | Cawood | A61B 10/007 600/580 |
| 2004/0241052 A1 | * | 12/2004 | House | A61B 10/007 422/400 |
| 2006/0184064 A1 | * | 8/2006 | Paasch | A61B 10/007 4/144.1 |
| 2014/0276214 A1 | * | 9/2014 | Lipinsky | A61B 10/007 600/573 |
| 2020/0397414 A1 | | 12/2020 | Aberbach | |

FOREIGN PATENT DOCUMENTS

GB 2162312 * 1/1986

* cited by examiner

*Primary Examiner* — Robert R Raevis
(74) *Attorney, Agent, or Firm* — Hanan Farber Patent Agent Ltd.

(57) ABSTRACT

The present invention discloses a fluid (e.g., urine) collecting vessel comprising a collector with an extension lip, wherein the collector is configured to fit inside a toilet with the extension lip placed on a toilet seat disposed on top of the toilet; a mechanism configured for extracting a sample of urine from inside the collector. The invention also disclosed methods for collecting fluids along a long time period comprising steps of providing a collector with an extension lip; placing the collector inside a toilet with said extension lip placed on a toilet seat disposed on top of the toilet; upon collecting urine inside the collector, extracting a sample of urine from inside the collector.

14 Claims, 25 Drawing Sheets

MEANS FOR COLLECTING SAMPLES OF URINE, DATA AND METHODS THEREOF

CROSS-REFERENCE TO RELATED APPLICATION

This application claims the benefit of U.S. Provisional Application No. 62/863,289, dated Jun. 19, 2019; and U.S. patent Ser. No. 16/904,665 dated Jun. 18, 2020, both are incorporated herein by reference.

FIELD OF THE INVENTION

The present invention generally pertains to means for collecting samples of bodily fluids and to methods thereof. The invention further relates with modules and kits for measuring and medical diagnostics. More specifically, the invention relates with a collector for animal' fluids, e.g., human urine, containers of the same, method of constructing and using the same, and methods for acquisition of data therefrom.

BACKGROUND OF THE INVENTION

Urine tests are used to monitor our health during our entire life. Urine monitoring is performed by healthcare organizations, enforcement agencies, sports organizations, research, etc. The most common urine tests are urinalysis, culture and urine collection over a 24-hour period. Twenty-four-hour urine collection is the recommended method of measuring substances such as sodium, potassium and protein intake but is logistically difficult and burdensome for participants at the population level, see John K A, Cogswell M E, Campbell N R, Nowson C A, Legetic B, Hennis A J, Patel S M. Accuracy and usefulness of select methods for assessing complete collection of 24-hour urine: a systematic review. *J Clin Hypertens.* 2016; 18:456-467; Institute of Medicine. Dietary Reference Intakes For Water, Potassium, Sodium, Chloride, and Sulfate. Washington, D.C.: *National Academy Press;* 2005; and Oria M, Yaktine A L, Strom B L. Sodium Intake in Populations: *Assessment of Evidence. Washington, D.C.: National Academies Press*; 2013.

Samples of long urine collections, in which urine is collected over time periods e.g. 6 hours, 12 hours, 24 hours, 48 hours, termed also "long collection", are mainly used to measure volumes of various substances (such as protein) or to monitor body-fluid balance. Tracking variations in urine substances (such as calcium) over long time periods, usually requires patient's hospitalization.

The scale of urine tests is constantly growing as, in addition to the above, urine tests are used to check adherence to prescribed medications, detect diseases such as cancer and they play an increasing role in home healthcare monitoring. Urine tests may be interpreted immediately or in laboratories. Immediate diagnostics are mainly performed by urine dipsticks. When reacting with urine, chemicals in the dipsticks' pads may change color. The colors are compared to a scale indicating status of the tested substance. Current urine sample collection methods for independent people (free from diapers or catheter) are tedious and unaesthetic. People may be required to target their urine flow into a small cup or test tube, then bring the urine cup or the test tube to a clinic. People may be embarrassed carrying the urine cup and try to cover or hide it. Some are asked to pour the urine into a test tube when vacuum test tubes are not used. Inconvenience only grows when a person needs to perform a long urine collection and collect all her/his urine during a long collection time period. Carrying a collection bottle. e.g. ajar with removable cap to work/studies/errands is embarrassing and unpleasant, and the person may choose to stay at home. In addition, the person is confronted with unpleasant smells, urine spilling, weight of collection bottle. Depending on the protocol used, after completing the long urine collection, the person may bring the bottle to a clinic or pour urine from the jar to a small urine cup or test tube, bring the cup or the test tube. In order to fill a small cup or a test tube, the collected urine in the bottle should be mixed. Holding the jar and shaking it in order to blend the urine is heavy, unpleasant and might result in spilled urine. Total urine volume collected in 24-hours may be 0.8 to 2.0 liter and in special cases up to four liters. Sometime the bottles used for long urine collection are small and more than one bottle is used. If the clinic requires the urine sample in a small cup or a test tube, the person may be requested to read and note the total urine volume in the bottles, shake them and pour urine to a small cup in a volume proportional to the volume in each bottle, an error prone process.

In order to provide a urine sample for a culture test, the initial urine flow is not collected. A person may be instructed to first urinate into the toilet, then stop urine flow, take a small cup and urinate into the cup. Naturally this instruction is challenging for children, elderly people, pregnant women, sick people, disabled people and caregivers. Due to difficulties in urine collection processes, adherence level with urine tests is low. Adherence is especially low with the 24-hour urine collection. In addition, many samples are rejected due to flaws in the long collection method, such as improper collection, improper urine mixing, missing information on the total urine volume which is essential for calculating volumes of substances (such as protein) in the urine. Therefore, in order to increase adherence, there is a need for a urine collection device that allows the user to naturally urinate (not into a small cup), without having to stop during the urination, obtain the urine sample easily and esthetically, without pouring or smelling the collected urine, a method which allows tracking and acquiring urine related data and without having to stay at home during long urine collections. There is a need to ensure the quality of the urine samples in order to avoid medical mistreatment.

SUMMARY OF THE INVENTION

It is an object of the invention to disclose a fluid (e.g., urine) collecting vessel comprising a collector with an extension lip, wherein the collector is configured to fit inside, or on top of a toilet with the extension lip placed on a toilet seat disposed on top of the toilet; a mechanism configured for extracting a sample of urine from inside the collector.

It is an object of the invention to disclose a vessel as defined above, wherein the vessel further comprising a socket configured to receive a sealed container with a seal; wherein the sealed container is insertable into the socket to penetrate the seal by the socket prior to extracting the sample of urine into the sealed container.

It is another object of the invention to disclose a vessel as defined in any of the above, wherein collector comprising a first set of compartments; and a mechanism configured to separate initial urine volume provided by a first urine flow, at at least one first compartment, from subsequent urine volume provided from a second urine flow, into at least one second compartment, further wherein only the subsequent urine volume of the at least one second compartment is extracted.

It is another object of the invention to disclose a vessel as defined in any of the above, wherein the collector comprises a hollow sleeve disposed either inside or outside the collector; wherein urine disposed inside the collector and inside the sleeve attain the same fluid level responsive to a fluid passage between the collector and the sleeve at the bottom of the collector; the vessel further comprising a mechanism configured for closing fluid passage between the collector and the sleeve upon collecting the sample of urine; and wherein the volume of urine extracted from the sleeve is proportional to the urine collected inside the collector with a known proportionality constant.

It is another object of the invention to disclose a vessel as defined in any of the above, wherein the collector comprises a detachable container disposed either inside or outside the collector; wherein urine disposed inside the collector and inside the container attain the same fluid level responsive to a fluid passage between the collector and the container at the bottom of the collector; the container further comprising a mechanism configured for closing fluid passage between the collector and the container upon detaching the container; and wherein the volume of urine in the container is proportional to the urine collected inside the collector with a known proportionality constant.

It is another object of the invention to disclose a vessel as defined in any of the above, wherein a plurality of urine samples obtained from subsequent sessions of urinations, is extracted from the sleeve are transferred to the receptacle; wherein urine accumulated in the receptacle is proportional to a total volume of urine collected during the previously determined time period with the known proportionality constant.

It is another object of the invention to disclose a vessel as defined in any of the above, wherein a plurality of urine samples obtained from subsequent sessions of urinations, that filled the detachable container are transferred to the receptacle; wherein urine accumulated in the receptacle is proportional to a total volume of urine collected during the previously determined time period with the known proportionality constant.

It is another object of the invention to disclose a vessel as defined in any of the above, wherein the receptacle further comprising a sensor configured to measure a parameter of the urine accumulated in the receptacle.

It is another object of the invention to disclose a vessel as defined in any of the above, wherein the receptacle further comprising a dipstick drawer in the receptacle, wherein the dipstick drawer is configured to receive a dipstick.

It is another object of the invention to disclose a vessel as defined in any of the above, wherein the dipstick drawer is configured to stream a portion of the urine that enters the receptacle into the dipstick drawer to immerse the dipstick.

It is another object of the invention to disclose a vessel as defined in any of the above, wherein the receptacle further comprising a transparent face of a receptacle, wherein an image of the urine is captured through the transparent face of the receptacle.

It is another object of the invention to disclose a vessel as defined in any of the above, wherein the container further comprising a dipstick drawer in or on the container, wherein the dipstick drawer is configured to receive a dipstick.

It is another object of the invention to disclose a vessel as defined in any of the above, wherein the container further comprises a mechanism to stream a portion of the urine that enters the container into the dipstick drawer to immerse the dipstick. Such as immersion is alternatively provided wetting the dipstick with urine by applying capillary driving forces.

It is another object of the invention to disclose a vessel as defined in any of the above, wherein the container further comprising a transparent face, wherein an image of the urine is captured through the transparent face of the container.

It is another object of the invention to disclose a vessel as defined in any of the above, wherein the container further comprises two compartments, a first fluid (e.g., urine) containing compartment and a second receptacle. The container is inserted into a socket. By applying vacuum, pressure or sub-pressure within the sealed container, flow of fluid is facilitated from the socket into a first compartment. The vessel further comprises a mechanism configured for transferring fluid to a second compartment. Hence, a plurality of fluid samples is collected from subsequent sessions of urination, and are flown from the socket to the first compartment, then and transferred to second compartment, the receptacle. Fluid accumulates in receptacle in a proportional manner up to a total volume of fluid that was collected during a predetermined period of time, in a defined volume proportionality constant.

It is another object of the invention to disclose a vessel as defined in any of the above that further comprises a sleeve in the collector. The container is insertable into the sleeve of the collector. It further characterized by an open-close shutting mechanism, configured for closing fluid flow between the collector and sleeve to allow flow of fluid from the sleeve into one compartment of container. Container further comprising a mechanism configured for transferring the fluid to the second compartment; Hence again, a plurality of fluid samples is collected from subsequent sessions of urination, and are flown from the sleeve to the first compartment, then and transferred to second compartment, the receptacle. Fluid accumulates in receptacle in a proportional manner up to a total volume of fluid that was collected during a predetermined period of time, in a defined volume proportionality constant.

It is another object of the invention to disclose a vessel which further comprises a container and a receptacle, both disposed either inside or outside the collector. Fluid (e.g., urine) disposed inside the collector and inside the container attains a same fluid level responsive to a fluid passage between collector and container at the bottom of the collector. Volume of urine held in container is proportional to urine collected inside collector with a known proportionality constant. Container further comprises a mechanism for transferring urine to the receptacle and for closing fluid passage between collector and container upon transferring fluid to the receptacle. A plurality of urine samples from subsequent urinations is transferred from the container to the receptacle. Urine accumulates in receptacle is in a proportional manner to the total volume of urine collected during previously determined period of time with a defined volume proportionality constant.

It is another object of the invention to disclose a sub-pressure actuated sample container. The sample container utilizes a pipette-mechanism to extract fluid from either collector or collector socket. The sample container further comprises a shutting-mechanism configured for closing fluid passage between collector and socket, if and when exists.

It is another object of the invention to disclose a vessel as defined in any of the above. In this embodiment, after a fluid sample is collected from the collector, possible mechanism to empty remaining fluid volumes from the collector is enabled by one or more members of a group consisting of (i)

a member in the collector; (ii) an extracting member; (iii) both the extracting member and a corresponding member in the collector.

It is another object of the invention to disclose a method for collecting fluids comprising steps of providing a collector with an extension lip; placing the collector inside a toilet with the extension lip placed on a toilet seat disposed on top of the toilet; upon collecting urine inside the collector, extracting a sample of urine from inside the collector.

It is another object of the invention to disclose a method as defined above, wherein the method further comprising steps of providing a socket configured to receive a sealed container with a seal; inserting the sealed container into the socket thereby penetrating the seal by the socket prior to extracting the sample of urine into the sealed container.

It is another object of the invention to disclose a method as defined above, wherein the method further comprising steps of providing a detachable container disposed on the collector wherein the volume of urine in the container is proportional to the urine collected inside the collector with a known proportionality constant.

It is another object of the invention to disclose a method as defined in any of the above, wherein the method further comprising steps of providing the collector with a plurality of compartments; separating an initial urine flow from a subsequent urine flow; the extracting of the sample of urine is provided only from a compartment including the subsequent urine flow.

It is another object of the invention to disclose a method as defined in any of the above, wherein the method further comprising steps of providing the collector with a hollow sleeve disposed inside or outside the collector, wherein urine disposed inside the collector and inside the sleeve attain a same fluid level responsive to a fluid passage between the collector and the sleeve at the bottom of the collector; upon the collecting of the urine sample, closing a fluid passage between the collector and the sleeve; extracting a volume of urine contained in the sleeve, wherein the volume of urine extracted from the sleeve is proportional to the urine collected inside the collector with a known proportionality constant.

It is another object of the invention to disclose a method as defined in any of the above, wherein the method further comprising steps of providing the collector with a detachable container disposed inside or outside the collector, wherein urine disposed inside the container and inside the sleeve attain a same fluid level responsive to a fluid passage between the collector and the container at the bottom of the collector; upon the detaching of the container, closing a fluid passage between the collector and the container; wherein the volume of urine in the container is proportional to the urine collected inside the collector with a known proportionality constant.

It is another object of the invention to disclose a method as defined in any of the above, wherein the method further comprising repeating the steps of collecting the urine sample and the extracting the volume of urine contained in the sleeve a plurality of instances during a previously determined time period; for all the instances, transferring a volume of urine contained in the sleeve to a receptacle, wherein urine accumulated in the receptacle is proportional to a total volume of urine collected during the previously determined time period with the known proportionality constant.

It is another object of the invention to disclose a method as defined in any of the above, wherein the method further comprising repeating the steps of collecting the urine sample and the extracting the volume of urine contained in the detachable container a plurality of instances during a previously determined time period; for all the instances, transferring a volume of urine contained in the container to a receptacle, wherein urine accumulated in the receptacle is proportional to a total volume of urine collected during the previously determined time period with the known proportionality constant.

It is another object of the invention to disclose a method as defined in any of the above, wherein the method further comprising steps of providing a sensor in the receptacle; measuring by the sensor a parameter of urine accumulated in the receptacle.

It is another object of the invention to disclose a method of extracting data from collected fluids, comprising steps of providing a fluid in a connection with a sensor configure to analyze at least one parameter, reading said analysis result(s) and transferring the same to a remote location for further processing, wherein said fluid is accumulated then analyzed is in proportional manner in respect to a total volume of the fluid collected known proportionality constant along a predefined long period of time.

It is another object of the invention to disclose a communicating system for extracting data from collected fluids, comprising means and modules as defined in any of the above for providing a fluid in a connection with a sensor configure to analyze at least one parameter, reading the analysis result(s) and transferring the same to a remote location for further processing, wherein the fluid is accumulated then analyzed is in proportional manner in respect to a total volume of the fluid collected known proportionality constant along a predefined long period of time.

It is another object of the invention to disclose a method as defined in any of the above, wherein the method further comprising steps of providing a dipstick drawer in the receptacle and a dipstick in the dipstick drawer.

It is another object of the invention to disclose a method as defined in any of the above, wherein the method further comprising steps of streaming by said dipstick drawer a portion of urine that enters into said receptacle and into said dipstick drawer thereby immersing said dipstick.

It is another object of the invention to disclose method as defined in any of the above, wherein the method further comprising steps of capturing an image of the urine through a transparent face of the receptacle.

It is another object of the invention to disclose a method as defined in any of the above, comprising steps of providing a container with one or more dipstick drawers and affixing the same in or on the container. Another step is configuring the dipstick drawer by means of size and shape to receive a dipstick.

It is another object of the invention to disclose a method as defined in any of the above, wherein the method further comprising a step of providing the container with a mechanism of streaming a portion of the urine that enters the container into the dipstick drawer, thereby to immerse the dipstick. Such as immersion is alternatively provided by wetting the dipstick with urine by applying efficient capillary driving forces.

It is another object of the invention to disclose a method as defined in any of the above, wherein the method further comprising a step of providing the container with a transparent face, so that an image of the urine is capturable through the transparent face of the container.

It is another object of the invention to disclose a method of a vessel as defined in any of the above, wherein the method further comprising a step of providing the vessel with two compartments, a container and a receptacle. A further step of inserting the container into a socket of the collector is provided. A further step of extracting or otherwise flowing the fluid from the socket into one compartment of container is also provided. A step of providing the container with a mechanism for transferring the fluid to the second compartment is also provided. This method comprises steps of extracting or otherwise flowing a plurality of urine samples from subsequent sessions of urination from the collector socket to one compartment of the container, then transferring the same to the other compartment, the receptacle. In this method, urine accumulated in receptacle is proportional to a total volume of urine collected during said previously determined time period with a defined proportionality constant.

It is another object of the invention to disclose a method of a vessel as defined in any of the above, wherein the method further comprising a step of providing the vessel with two compartments, a container and a receptacle, and a corresponding sleeve-like container in the collector. In this method, a step of inserting a container into a sleeve of the collector is provided. A step of providing the container with a mechanism for shutting fluid passage between the collector and sleeve is provided useful for extracting fluid from the sleeve into one compartment of container. A step transferring the fluid to the second compartment is also provided. This method also comprises steps of extracting or otherwise flowing a plurality of urine samples from subsequent sessions of urination from the collector socket to one compartment of the vessel, the container, then transferring the same to the other compartment, the receptacle. In this method, urine accumulated in receptacle is proportional to a total volume of urine collected during said previously determined time period with a defined proportionality constant.

It is another object of the invention to disclose method of a vessel further comprising a container and a receptacle, both disposed either inside or outside the collector; wherein urine disposed inside said collector and inside said container attain the same fluid level responsive to a fluid passage between collector and container at the bottom of the collector; wherein volume of urine held in container is proportional to urine collected inside collector with a known proportionality constant. Container further comprising a mechanism for transferring the urine to the receptacle and for closing fluid passage between collector and container upon transferring the fluid to the receptacle; wherein a plurality of urine samples from subsequent urinations, are transferred from the container to the receptacle; wherein urine accumulated in receptacle is proportional to a total volume of urine collected during previously determined time period with the known proportionality constant.

It is another object of the invention to disclose a method as defined in any of the above. The method comprises steps of utilizing a pipette mechanism for facilitating the flow of fluid from either collector or the socket. The method also comprises steps of shutting or otherwise closing fluid flow from the collector and the socket, if and when exists.

It is another object of the invention to disclose a method as defined in any of the above for extracting or otherwise flowing the remaining volume in the collector after a urine sample was collected from the collector. By this method, emptying of the fluid from the collector is configured by either (i) providing and actuating a member in the collector (ii) providing and actuating extracting member (iii) by both providing and actuating extracting member and a corresponding member in the collector.

BRIEF DESCRIPTION OF THE DRAWINGS

The invention is herein described, by way of example only, with reference to the accompanying drawings, wherein.

BRIEF DESCRIPTION OF THE PREFERRED EMBODIMENTS

Figure 1A:
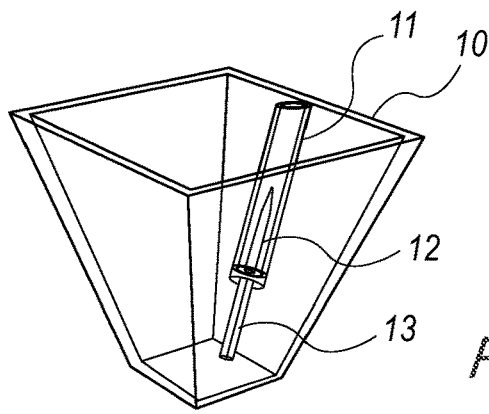
FIGS. 1A, 2A, 3 and 4 present respectively perspective view, top view, front view and side views of a first embodiment of a collector, according to certain features of the present invention.
Figure 2A:
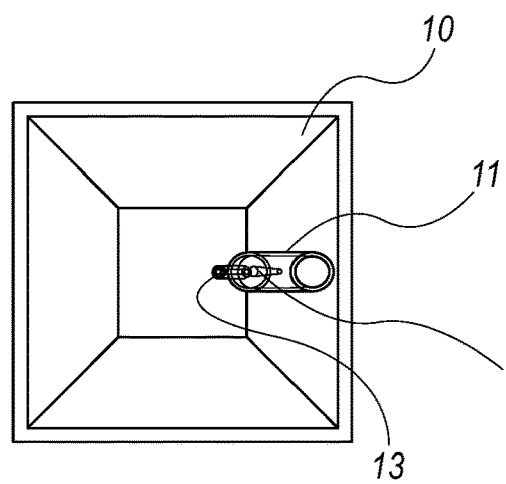
Figure 3:
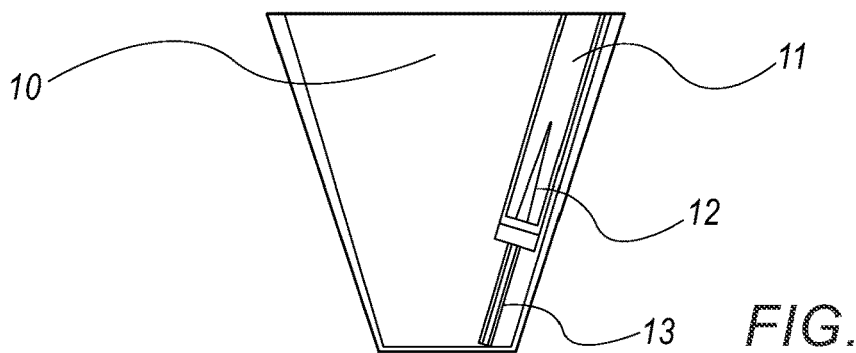
Figure 4:
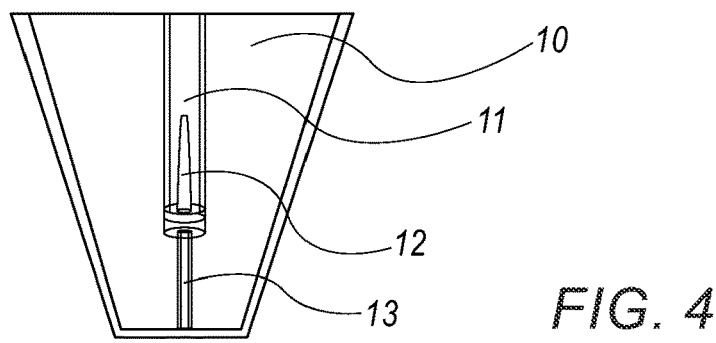

The invention will now be described in detail in connection with certain preferred and optional embodiments, so that various aspects thereof may be more fully understood and appreciated.

By way of introduction, an object of the invention is to improve urine testing for healthcare monitoring, enforcement, sports or the like. In addition to collection of the urine sample; objects of the invention are to enable tracking, collecting, physiological, chemical and biological data acquisition and data-based user guiding. Disclosed embodiments of the invention allow user to easily and esthetically collect one or more urine samples for a urine test, e.g. urinalysis, culture, 24-hour urine collection, and either interpret the hereto collected data immediately and/or subsequently, whereas Data interpretation is provided either in situ, or at a remote location, such as a point of care, laboratory etc.

The collector, modules and kits thereof disclosed hereinafter enable users for both easy and esthetic collection of samples of fluids for either or both online or offline diagnosis.

It is hence in the scope of the invention wherein a collector is placed inside or on top of a toilet with an extension lip placed on a toilet seat, and disposed on top of the toilet. Upon collecting urine inside the collector, outflow of a metered dose volume of urine is facilitated.

In another embodiment of the invention, a collector comprises a socket, configured to receive a sealed container of either (i) a predefined or (ii) measurable, adjustable or otherwise determinable volume. It is acknowledged in this respect that the hereto underlined container is selected from either sealable or non-sealable members, namely to vacuum-tubes, syringe-like test tubes, regular sample tubes, and for any other suitable type of tubes. The sealed or non-sealed container is configured, by means of size and shape, to be reversibly insertable within collector's socket, thereby to puncture or otherwise penetrate the seal, then to allow an outflow of a metered dose sample of urine form the collector to the container. Alternatively, instead of inserting a container to a collector socket, the container is provided as filling member, attachable to the collector and detached once filled with the desired volume.

In another embodiment of the invention, a collector comprises multiple compartments. Such a compartmentability allows to facilitate a quantitively defined volume inflow of a first (initial) urine to a at least one first compartment, and to separable the same of a second (latter) urine inflow, directed to at least one second compartment. The latter urine inflow then selectively enabled to flow to the second compartment, hence to sample a metered dose volume of the hereto obtained secondary urine flow without allowing a mixture or contamination of this latter flow with or by the initial flow.

A system of communicating vessels comprises multiple containers filled with a fluid, connected at the base and subjected to the same atmospheric pressure. When the liquid settles, it balances out to the same level in all of the containers regardless of their shape and volume. If additional liquid is added to one vessel, a new equal level will be established in all the connected vessels. It is hence another embodiment of the invention, where a first vessel, i.e., a collector is in either (i) a free or (ii) controlled fluid connection with a second sleeve-like vessel, shaped as pipe, tube, hose, conduit, or otherwise an elongated hollow compartment (hereinafter "sleeve"). At least one sleeve is disposed either or both inside or outside the collector. Urine inflow is directed towards the sleeve via the collector. Sleeve attains a same fluid level responsive to a fluid passage between the collector and the sleeve. Upon collecting a urine sample, fluid's free flow between the collector and the sleeve is shut. The volume of urine contained in the sleeve is then out flown. The term "receptacle" refers mainly yet in a non-limiting manner to a vessel configured to store fluids, such as a sample of urine or overall urine obtained in a defined period of time.

It is in the scope of the invention wherein the volume of urine evacuated from the sleeve is proportional to the overall volume of urine collected within the collector. In another embodiment of the invention, proportionality is either constant or definable. In this manner, urine samples are repeatedly collected along the period of time, e.g., 24-hour period.

In another embodiment of the invention, a volume of urine contained in the sleeve is transferrable to a receptacle. Urine accumulated in the receptacle is hence proportional to a total volume of urine collected during the previously determined time period with a known proportionality constant.

A urine test strip or dipstick is a basic diagnostic tool used to determine pathological changes in a patient's urine in standard urinalysis. A standard urine test strip may comprise up to dozen different chemical pads or reagents which react, e.g. change color, when immersed in, and then removed from, a urine sample. The test can often be read in as little as one or two minutes after dipping, although certain tests require longer. The analysis includes, inter alia, testing for the presence of proteins, glucose, ketones, hemoglobin, bilirubin, urobilinogen, acetone, nitrite and leucocytes as well as testing of pH, specific gravity or to test for infection by different pathogens, test for pregnancy or drugs In thus another embodiment of the invention wherein the receptacle comprises one or more types of biological, chemical or physical detectors, test strips, or otherwise "sensor(s)", each of which is configured to measure a relevant parameter of the hereto collected urine. According to another embodiment of the invention, receptacle comprises or is provided in a fluid connection with a urine test strip. The dipstick may be provided in a dipstick's drawer-like compartment into which a portion of inflowing urine is wetting, immersing or otherwise provided in an effective contact with the dipstick. Image of the dipstick or sensor outcome(s) is/are visible via receptacle's wall.

According to exemplary embodiments of the present invention, the system may include two parts: a collector for collecting urine samples and a receptacle into which urine samples are later stored and possibly analyzed. For a urine sample, for single and/or long urine collections, the present disclosure provides a small and esthetic product that can be easily placed in a bag. The user may attach the collector to a toilet seat, may urinate in a natural mode (either sitting or standing) and may extract the urine sample into a sealed container, e.g. an evacuated tube, a culture device. The user may provide the sealed container to healthcare, enforcement or sports unit for further immediate and/or subsequent laboratory testing. Alternatively, the user may transfer the urine sample from the tube into a receptacle, for temporary storage and accumulation of all urine samples during long, e.g. 24-hour urine collections. The terms "toilet" and "bin" are used herein interchangeably and refer to any of a flush toilet connected to sewage drain; or, a portable commode, a toilet chair, a portable toilet, and/or a bedside commode which are not permanently connected to a sewage drain.

The terms "sealed container" and "sample container" are used herein interchangeably.

The term "parameter" as used herein in the context of accumulated urine may refer to urine level, volume, weight, an amount of one or more substances included in the accumulated urine.

Although selected features of the present invention have been shown and described, it is to be understood the present invention is not limited to the described features.

New collector and receptacle embodiments for collecting urine samples and related data are discussed herein. For purposes of explanation, numerous specific details are set forth in order to provide a thorough understanding of the present disclosure. It will be evident, however, to one skilled in the art that the present disclosure may be practiced without these specific details.

This disclosure allows the user to run immediate diagnostics without having to pour, smell, dip-into urine and with no medical staff assistance. This disclosure allows the user to provide a sample for culture test, by urinating freely with no disturbance. The user is free from the need to stop urinating, taking a cup and then proceed urinating. According to features of the present invention the user is freed from the need to collect all the urine given throughout long collections. Instead, at each urination throughout the long collection, a small urine volume is collected, proportional to the urine volume given at each urination. The receptacle includes a special container into which the urine sample of each urination is collected. Once the long urine collection is complete, the receptacle holds a true representation of the entire urine given throughout the long collection. The user easily obtains a sealed test tube (or a similar container) holding the urine sample of the long collection for either immediate diagnostics and/or further lab tests. Data (user ID, time stamp, volume, various chemical and pathological elements, etc.) may be collected by either hardware (sensors+IoT tools) or software, by photo capturing the receptacle and utilizing tools such as image processing. Data is transmitted over the network to both the monitoring authority (healthcare or other) and the user. An application may enable tracking, detection and user guidance. This disclosure is directed to free the user from the necessity to manually pour the urine into a small cup, a jar, a tube (or the like) and seal it, from having to manually measure the urine volume or manually track and report urine sample related data. The user can easily carry both the collector/s and the sealed receptacle in a handbag or the like, enjoy regular undisturbed daily routine when performing a long urine collection. The user is both guided along the collection process, updated and advised on the urine test results. Medical staff work becomes more efficient due to a higher quality of the urine samples and are partially freed from a tedious task. Embodiments of the disclosure enable continuous tracking of variations in urine substances (such as calcium) during many hours, without having to hospitalize the patient but rather allow the patient to enjoy regular undisturbed daily routine. Objects of the disclosure include providing a collector that enables obtaining a tube (or a similar container) without handling urine (handling is: targeting, pouring, spilling, touching); providing a portable device to accumulate a fractional volume proportional to urination volume during a time period; providing a system to separate between initial urine and the rest without contaminating the sample; providing a device that allows immediate diagnostics without handling urine; providing a portable container to collect several tubes (or similar containers) and mark their order, therefore; offering a new approach of detecting variations in urine substances using sensors or image capturing of the receptacle for volume and an additional parameter of accumulated urine; freeing the user from storing and carrying a closed bottle of urine during long collection time periods and instead storing a proportional urine samples in a portable, aesthetic and small receptacle which may be provided in a small portable bag with several folded/squeezed small collectors and a receptacle to allow mobility.

Embodiments of the present invention are directed to urine collection and tracking; however, variations may be directed to collecting and analyzing fluid content such as human breast milk, animal milk and agricultural oriented fluids.

As said above, a urine sample container is presented here as a vacuum test tube. However, the sample could be obtained by any other sub-pressure activated tube, such as a syringe or a pipette or could be a detachable tube.

Reference is now made to FIGS. 1A, 2A, 3 and 4, Each of which Schematically illustrates in an out-of-scale manner a perspective view, top view, front view and side view, respectively, of animal fluid's (e.g., human urine, fecal, purges etc.) collector 10, according to an embodiment of the invention. Collector 10 is configured for serving either (i) in a disposable manner, being one-time used, or (ii), reusable. Collector and modules thereof are made of either or both disposable materials, including, polymers such as biopolymers, including, e.g., laminates and biodegradable corn starch, polylactic acid, polyglutamic acids, paper-ware or cellulose-containing materials, etc., and/or made of a durable reusable material, including glass-ware, metal-ware, polymer such as polyethylene, polypropylene, polyesters, polyamides, and any mixtures and combination thereof. Much similarly, it is in the scope of the invention wherein Collector 10 is at least partially made form dissolvable, dispersible, disintegrated or deconstructed materials after consuming, namely by reaction with acids, base, water, enzymes, surfactants etc.

It is well in the scope of the invention wherein the shape of collector 10 is at partially of either or both rectangular and/or rounded cross section, e.g., a rigid pyramid, a semi-flexible cone etc., or is at partially of a geometrically undefined shape, e.g., a flexible sack. Collector 10 bottom portion may be pre-designed as horizontally balanced or may achieve horizontal balance by the weight of fluid filling it. Collector 10 may hold up to about 1.2 liter or larger if needed of fluid, e.g. urine. The term "about" refers hereinafter to a value being greater than or smaller than up to 25% of the defined value. Collector 10 upper end may be open or covered by a material that either collects, absorbs or diffuses the urine in order to avoid fluid (urine or other) back-splashes. The cover is made of either a disposable, dis-soluble or a durable material.

Figure 9:
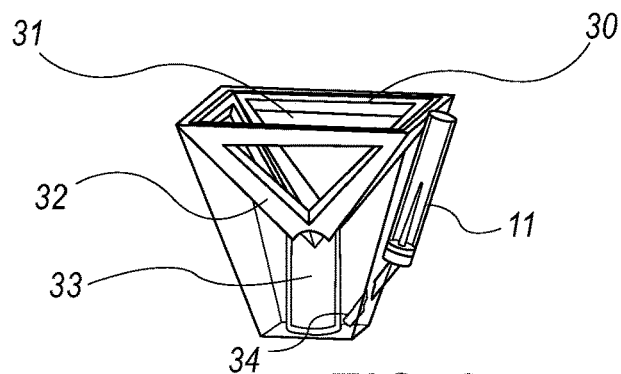
FIGS. 9, 10A/10B, 11 and 12 present respectively perspective view, two top views, front view and side view of an additional embodiment of a collector, according to certain features of the present invention.

Referring back to FIGS. 1A, 2A, 3 and 4, collector 10 has a main part and a pocket 11. Pocket 11 may be attached from either the inside as shown or outside as depicted in FIG. 9. Pocket 11 may be isolated from collector 10 and is open at its upper end to allow flow of air. A pipe 12 may extend through a narrow passage at the bottom of pocket 11 and may be connected to a feeding pipe 13 that extends from bottom of collector 10, through main part of collector 10, to bottom of pocket 10. Pipe 12 may be made of either a disposable, dissolving or a durable material. Pipe 12 may have sharp upper ends protected by a protrusion. During operation, urine is collected in collector 10, a sample container, e.g. an evacuated tube, may be inserted into pocket 11. A seal of the evacuated tube may be pierced by the sharp upper end of pipe 12 and may be filled with urine through the feeding part 12 of collector 10 and through feeding pipe 13. Alternatively, the sample container placed in pocket 11 may be filled by using another sub-pressure technique. Sub-pressure may be created by methods such as activating a simple piston (not shown) on collector 10. Once finished urinating, the user triggers the sample container to fill by applying light manual/powered force such as pushing, pulling or rotating. The air-evacuated sample container may be filled with urine once the top sharp end of pipe 12 penetrates the sample containers' seal at bottom of pocket 11 or following a piston activation on the sample container in pocket 11. Due to sub-pressure, the sample container in pocket 11 may be filled up to maximum volume capacity unless there isn't enough urine in the collector. The user obtains a clean, dry and sealed container, filled with the desired urine sample.

Figure 1B:
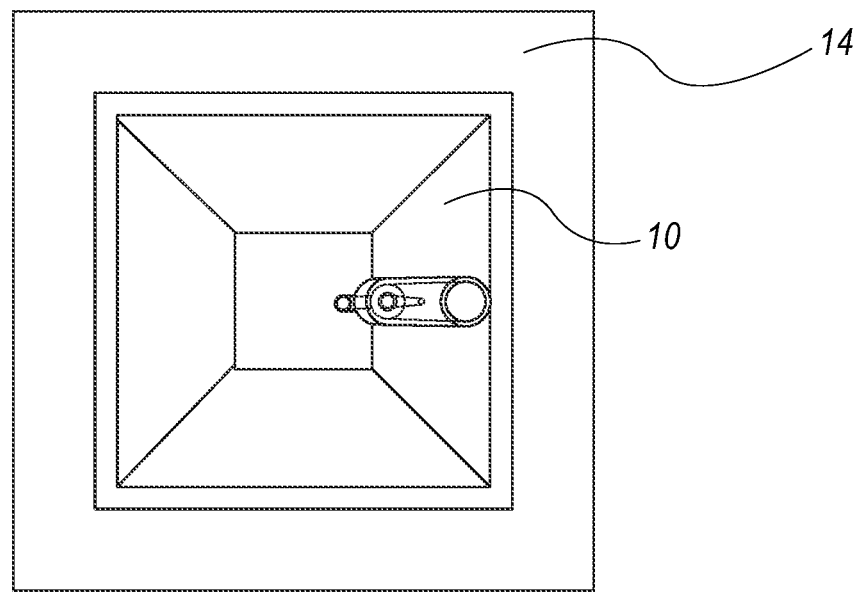
FIGS. 1B and 2B. present top and side views of the collector shown in FIGS. 1-4 and collector attachment extension for fitting over a toilet seat, according to certain features of the present invention.
Figure 2B:
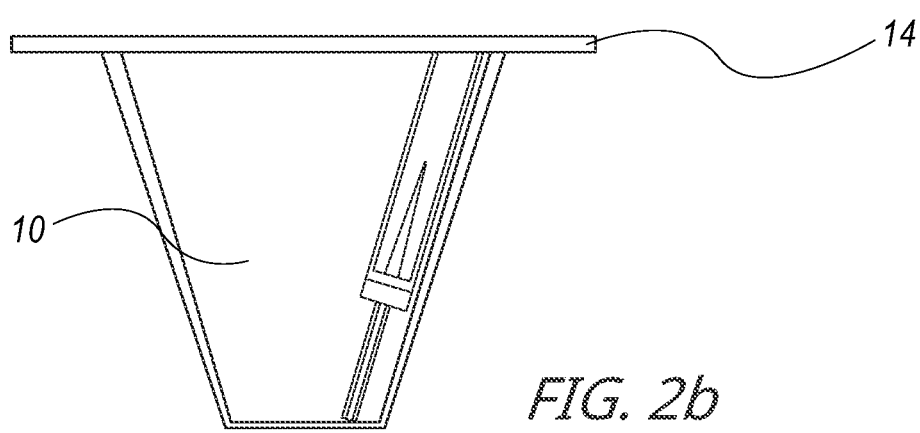

Reference is now made to FIGS. 1B and 2B, which illustrate top and side views of collector 10 and collector attachment extension 14 for fitting over a toilet seat, according to features of the present invention. The presented shape of collector attachment extension 14 is for explanatory purposes only, as extension 14 may be of any shape and not necessarily around all the perimeter of collector 10 upper part. Collector extension 14 may be placed on the toilet seat and may be attached either manually by using clips, bands or similar, or by utilizing a glue-like material to attach it to the toilet seat. Collector extension 14 is made, e.g., from either or both disposable or long-lasting materials, recycled compositions etc. Collector 10 is possibly detachable from the toilet seat, by either a manual/powered trigger or due to a adhesives and glue-like materials that dissolves after a pre-defined time or a chemical reaction. Then, by way of example, collector 10 may fall or flashed hence disposed into the toilet or bin.

Reference is now made to FIGS. 5 to 8 which depict respectively perspective view, top, front, and side views of a collector 20 of a second embodiment of the invention, that together with the receptacle described below, is designed to provide a urine sample of a long time-period urine collection. In each urination during the long time-period collection, user may use collector 20 and obtain a sealed sample container, e.g. evacuated tube, which holds urine in a volume proportional to urine volume given during that urination. To enable that, collector 20 comprises a main vessel 20 as in collector 10, and a sleeve 21 which comprises pocket-like vessel 11. Main part 20 and sleeve 21 are filled with urine in volumes proportional to their sizes as defined below. A sample container, e.g. an evacuated tube in pocket 11 is filled with urine in sleeve 21 which is transferred into the aforesaid receptacle. Sleeve 21 may be filled in a non-limiting manner by various systems such as communicating vessels or by applying a fluid distribution technique at the upper end of the collector. To enable a distribution mechanism based on the principle of connecting vessels, sleeve 21 has a small passageway, a feeding entry 22 between sleeve 21 and main part 20 of the collector. Therefore, urine in both parts: main chamber of collector 20 and sleeve 21, reaches to a same level. An exemplary alternative fluid distribution technique from the upper part of collector 20 is activated through a horizontally balanced membrane (not shown) stretched over the upper part of collector 20. Urine that flows into collector 20 is slightly detained by the membrane which is designed to allow an even fluid spreading. Therefore, those two parts of collector 20 hold urine in volumes being proportional to their volume capacities. As a result of either technique, sleeve 21 holds urine in a volume proportional to the total urine volume that filled collector 20. The urine volume collected in sleeve 21 is ready to be transferred to a sample container placed in pocket 11. Dimensions of collector 20 and sleeve 21 are configured to allow collecting one or more urine samples of both small and relatively bigger amounts, as well as meeting the maximum volume capacity of the container (a tube or similar) placed in pocket 11.

As sub-pressure techniques may be applied to fill the sample container in pocket 11 with urine in sleeve 21; the feeding passageway 22 is shut before filling. A plug may be created by a material that dissolves within a predefined time and seals passage 22 or by a seal that is already included in collector 20, triggered to block passageway 22 by means of controlling time, applying manual/powered force or allowing a chemical reaction with fluid (such as water, urine). An example to trigger by force is the action of pushing the sample container, e.g. evacuated tube in pocket 11 downwards that would first trigger the plug to close feeding passage 22.

Once feeding passage 22 is closed and a sub-pressure technique is used to fill the sample container placed in pocket 11, the volume of urine held in sleeve 21 is collected. The small collector is holding urine in a volume proportional to urine given at a specific urination may be emptied into the above disclosed receptacle. As all dimensions are known, the volume in the sample container indicates by simple calculations based on proportional volumes and minimal fluid loss, the total volume of the urine that filled the collector. This may be done in vitro, namely, in, or adjacent to the receptacle, namely in situ, online, offline, or by communication with hardware and software located in adjacent or remote location.

Figure 10A:
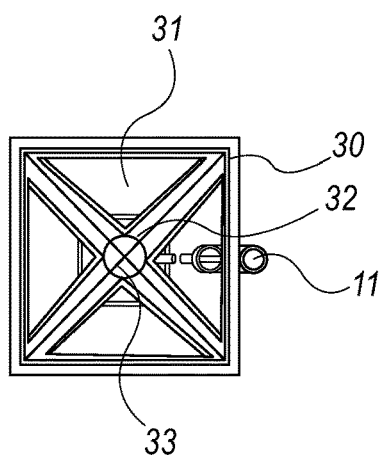
Figure 10B:
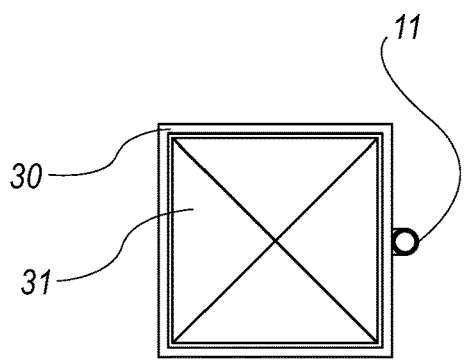
Figure 11:
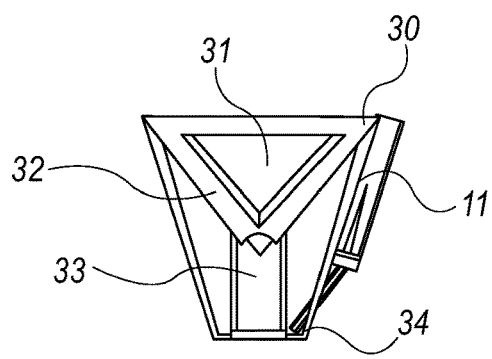
Figure 12:
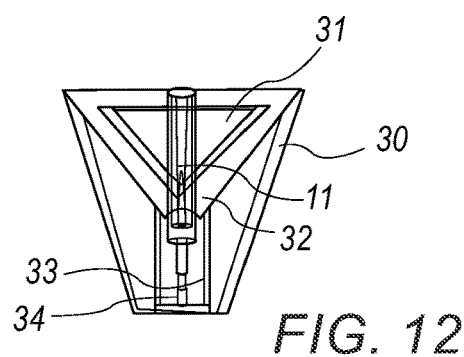
Figure 13:
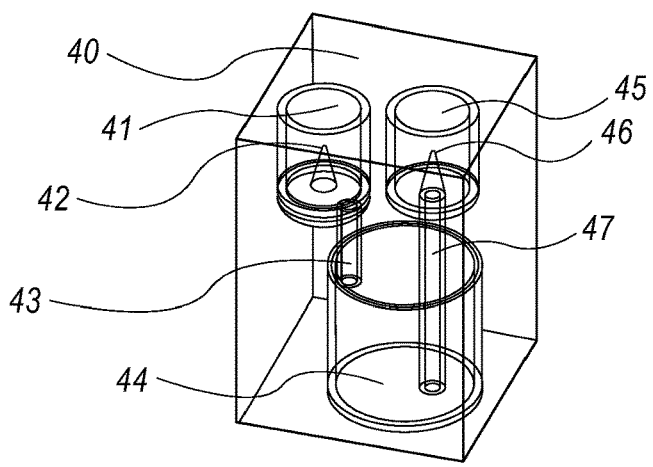
FIGS. 13 to 16 illustrate respectively perspective view, top view, front view and side views of an embodiment of a receptacle, according to certain features of the present invention.
Figure 14:
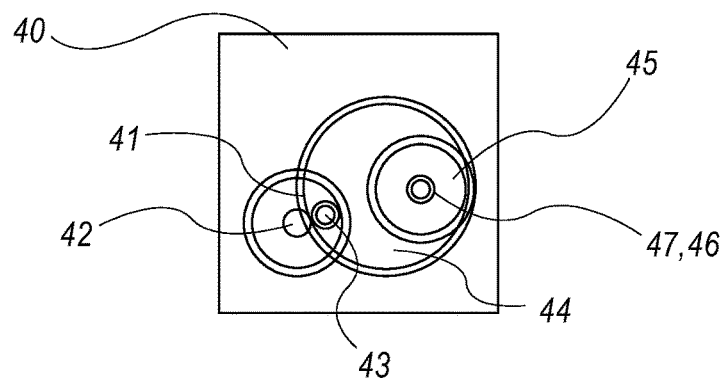
Figure 15:
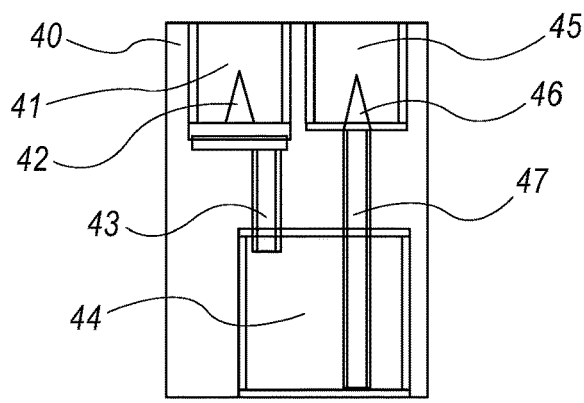
Figure 16:
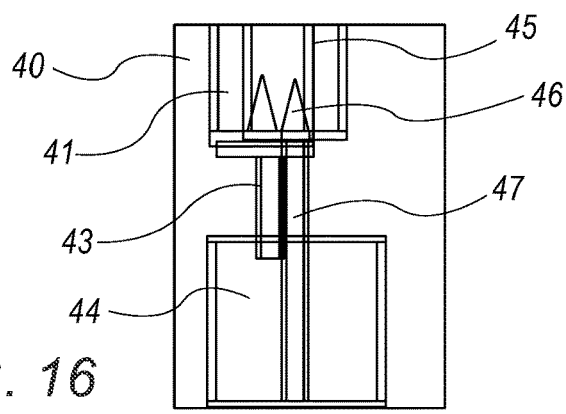
Figure 17:
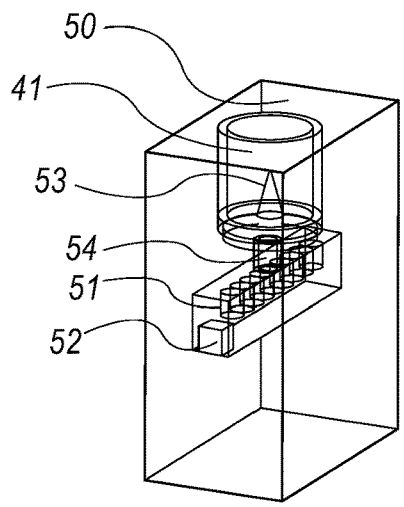
FIGS. 17 to 20 present respectively perspective view, top view, front view and side view of another embodiment of a receptacle, according to certain features of the present invention.
Figure 18:
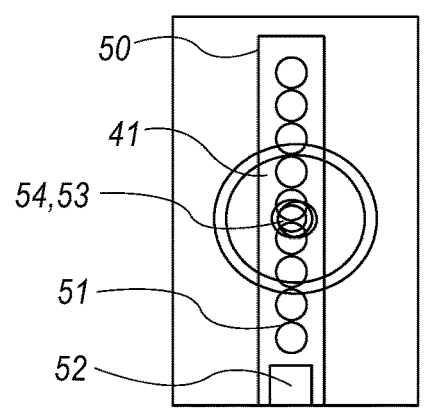
Figure 19:
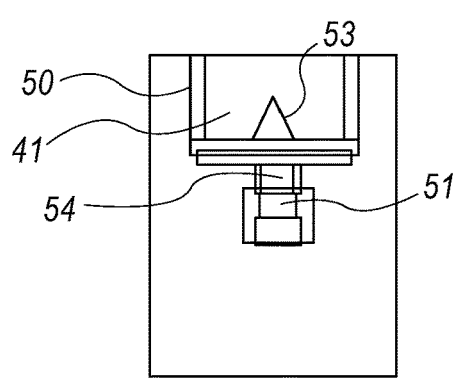
Figure 20:
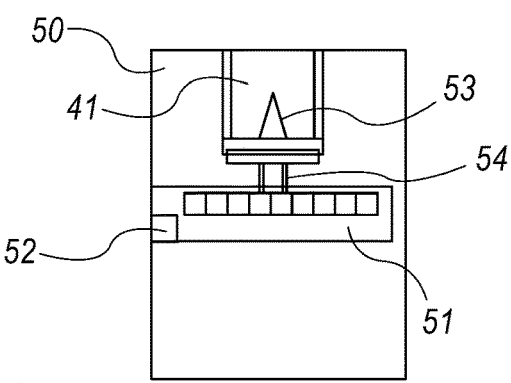
Figure 20A:
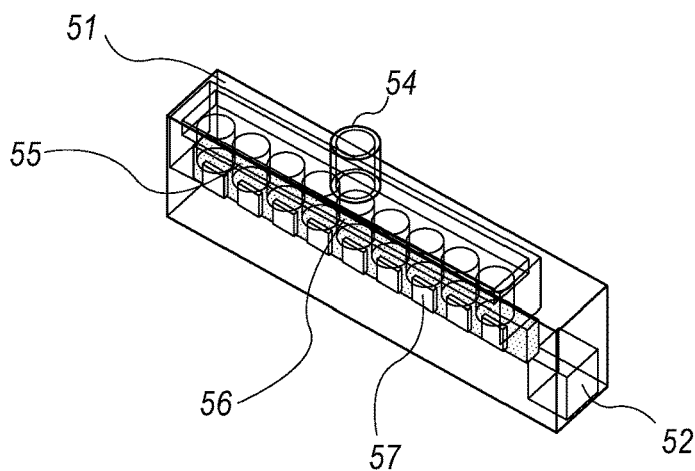
FIGS. 20A, 20B, 20C and FIG. 20D illustrate respectively perspective view, top view, front view and side view of a dipstick drawer according to features of the present invention.
Figure 20B:
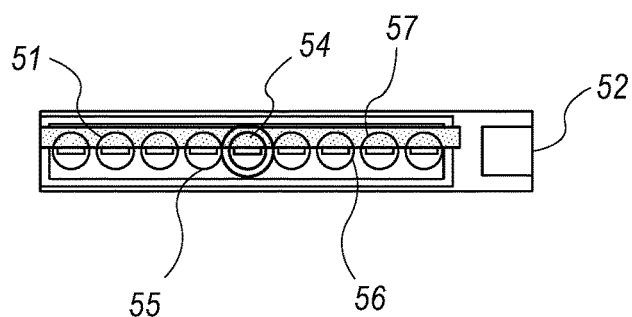
Figure 20C:
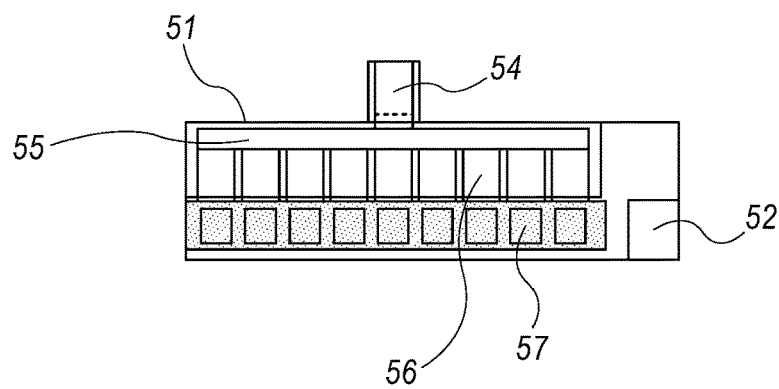
Figure 20D:
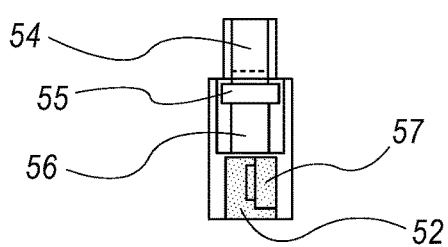

Reference is now made to FIGS. 9, 10A, 10B, 11 and 12 which illustrate respectively perspective view, two top views, front view and side view of collector 30, directed to collect a sample for urine culture tests. Collector 30 separates between initial urine flow and subsequent urine flow and provides a urine sample of only the latter. Pocket 11 is depicted as attached to collector 30 from the outside, yet it can also be attachable from inside. In exemplary embodiments, collector's 30 upper perimeter is attached to and covered by container 31. Container 31 is intended to collect an initial urine, as depicted in FIG. 10B. Container 31 is made of e.g., a flexible composition or a material affected by weight, and its bottom end is placed in pipe 33 as depicted in FIG. 9. Pipe 33 is shown, e.g., in the middle of collector 30, however pipe 33 may be alternatively positioned closer to collector 30 walls. Urine weight causes container 31 to sink into pipe 33. At a pre-defined weight, the pressure may cause container 31 upper edge to tear along a tearing line(s) in a controlled manner, assuring that the initial urine flows only into container 31 and pipe 33 in a selective manner, namely not into any other part of container 30. A possible tearing technique is applied by a thread that runs along the attachment of collector 30 and container 31. The thread lower-end lies at the bottom of container 31. Urine weight causes container 31 to sink into pipe 33 and apply a pulling-force towards the thread, resulting in detachment of container 31 from collector 30, and provides its sinking into pipe 33. Pipe 33 bottom portion may be either closed or open to remove initial urine flow. Pipe 33 dimensions and materials prevent urine overflow, diffusion etc. that could mix between the initial urine and the rest. Pipe 33 may be attached or otherwise fastened to collector 30, for example, by strips 32 that are revealed after sinking of container 31 into pipe 33. The rest of the urine, subsequent portion of urine after initial flow, flows into collector 30. Pocket 11 and the sample container, e.g. evacuated tube, may be fed through a feeding opening 34. Therefore, sample container may be filled with urine outwardly to pipe 33 that is neither contaminated by the initial urine flow, nor by urine that flowed over parts that might have been contaminated by the initial urine.

Reference is now made to FIGS. 13 to 16, illustrating in an out-of-scale manner perspective view, top view, front view and side view, respectively, of a receptacle 40, which may be configured for measuring and/or reporting urine volume collected during a long time-period collection and provide a urine sample of the collection. Receptacle 40 is directed to collect urine samples over long collections, store them, provide a urine sample of a long time-period collection and/or run immediate diagnostics on urine samples. A urine sample container containing a urine sample during a long time-period collection may be inserted into a feeding socket 41 and urine content therefrom is emptied into chamber 44. After each urination during a long time-period collection, user empties sample container, e.g. tube filled with urine, by inserting it in feeding socket 41 of receptacle 40.

A second insertion socket 45 is shown for final collection of a combined urine sample from the multiple samples during the long collection by inserting an empty sub-pressure activated sample container to transfer urine sample from chamber 44. In some embodiments the functions of filling chamber 44 and sampling from chamber 44 may be combined using a single socket 41 and 45.

Insertion of the sample container into socket 41, may trigger by either manual or powered force an action of seal 42. Seal 42 may comprise a mechanism for extracting or letting urine flow from the sample container and a valve that opens to let the urine sample flow from the sample container, through pipe 43, and fill receptacle chamber 44. Once completed, a manual or powered force may trigger seal 42 to close and eject the empty sample container.

In order to extract the urine from the sample container, seal 42 may have a piercing member that penetrates sample containers' seal. As this action is repetitive for long time-period collections, and in order to avoid contamination or mix of the hereto collected urine, the piercing member of seal 42 may be replaced at each insertion of a sample container. It is well in the scope of eth invention wherein seal 42 may has a fluid extracting mechanism compatible with the sample container, which could either be a sub-pressure activated tube, such as a syringe or a pipette or a sealed detachable tube. Hence for example, seal 42 may comprise a piercing member.

After such an event of emptying a sealed sample container into a receptacle chamber 44, a change in urine volume inside chamber 44 may be detected by either sensors or by image capturing of the receptacle, e.g., by having a transparent wall portion. This data and additional data such as time, user ID, is transmittable to a relevant monitoring unit at a remote location such as healthcare providers, enforcement and police officer, and user who may receive personal guidance.

It is hence well within the scope of the invention wherein mechanisms, systems and methods are presented and provided useful for extracting data from collected fluids, comprising step of providing a fluid in a connection with a sensor configure to analyze at least one parameter, reading the analysis result(s) and transferring the same to a remote location for further processing, wherein the fluid is accumulated then analyzed is in proportional manner in respect to a total volume of the fluid collected known proportionality constant along a predefined long period of time.

Upon completion of long time-period urine collection and before extracting a urine sample of the long collection, urine in chamber 44 may be mixed. User may gently shake receptacle 40 or chamber 44 is disposed with a mixing element for manual or powered mixing. User may insert a vacuum or pressure driving force to flow sample into receptacle socket 45 and fill the sample container through a sharp tipped pipe 46 and through the feeding pipe 47 with a urine sample that includes a mixer of all the urine samples collected in chamber 44 during the long urine collection. User may provide the filled sample container to the clinic for further diagnostics tests or if requested, provides the clinic with receptacle 40.

Reference is now also made to FIGS. 17 to 20 which illustrate perspective view, top view, front view and side view, respectively, of a receptacle 50, according to another exemplary embodiment of the present invention. This receptacle is configured for immediate diagnostics of the urine stored in the sample container, and may comprise a dipstick drawer 51 into which a diagnostic means, e.g., a dipstick may be inserted through a dipstick's insertion socket 52, which is otherwise sealed to avoid contamination or spills. Upon design, considerations for esthetic dipstick insertion and removal, the dipstick may be placed on a leading slide surface or in a box that is configured to be inserted throughout an insertion socket 52. In receptacle 50, as in receptacle 40, sealed sample container may be inserted in feeding socket 41 of receptacle 50 and triggers, by manual or powered force, an action of special seal 53, to extract or let flow of urine from the sealed sample container, stream it throughout pipe 54, to fill the dipstick drawer 51. Once completed, seal 53 is maneuvered or triggered to both close and eject the empty sample container.

In order to extract urine from the sample container, seal 53 comprises a sharp member that penetrates sample containers' seal. For a reusable receptacle 50, and in order to avoid contamination of the urine test, the sharp member of seal 53 may be replaced at each insertion of the sample container.

Reference is now made to FIGS. 20A, 20B, 20C and 20D which illustrate perspective view, top view, front view and side view, respectively, of a dipstick drawer 51. Dipstick 57, a slide, box or the like, holding and leading the dipstick into the dipstick drawer 51, is configured to be placed horizontally or vertically in drawer 51, and dipstick 51 may be immersed through pipes of various sizes, diffusion materials, wetting by capillary forces etc.

To emulate immersion of dipstick 57 in fluid, urine in dipstick drawer 51 may be held for a time to immerse dipstick 57. This may be done by streaming fluid at a suitable predefined pace, for example through detained diffusion using applicable materials. Then, urine flows to the bottom of drawer 51 to remove excess urine from dipstick 57. Additional time may be allowed for dipstick 57 chemical reactions to occur, and reflect a change of color. Urine effect on the dipstick may be measured by sensors or by image capture means of receptacle 50 which may have a transparent portion of a wall. This data and additional such as time, location, and user ID, is transmitted to both the relevant monitoring unit, and user who may receive personal guidance.

Reference is now made to FIG. 21 to FIG. 24, each of which illustrates another exemplary embodiment of receptacle 60, prospective view, top view, front view and side view, respectively. Receptacle 60 is aimed to collect urine samples of long urine collections and/or run immediate diagnostics.

Reference is now made to FIG. 25 to FIG. 28 each of which illustrates respectively perspective view, top view, front view and side view, of receptacle 70, according to yet other embodiment of the invention. Receptacle 70, a round or otherwise shaped receptacle is aimed to collect sample containers, tubes or the like, holding urine samples collected along long time-period of urine collections, in order to test the variations in urine substances during a long time period of urine collection. Unlike other embodiments, receptacle 70 doesn't store together the content of all the sample containers, as its purpose is to test the content of each urination sample along several hours. Therefore, it collects and stores the sample containers themselves.

It is in the scope of the invention wherein each sample container is provided by an identification mark to set their order, such as barcode, a QR etc. The sample containers are opened in a laboratory, to test and track variations in the urine substances during collection hours. Samples can also be tested by one or a plurality of immediate diagnostics' receptacle 50.

The receptacle entry socket 71 is used to insert the sample container which is configurable as a sample tube or the like. Once such a sample tube is inserted, it is identified or otherwise an identification mark is appended to set its order. Tube insertion triggers former tubes to move to a notch in 72, an area in which containers are stored. Marking (identifying) and advancing mechanisms of the containers in 72 are providable in one or more suitable manners. For example, sample tubes are loaded into volume 72 in a mechanism similar to loading fire-cartridges into a magazine.

The dimensions of volume 72 are designed to allow storing all of the containers used throughout long time-period collections. The order of the sample tubes is detectable by sensors or by photo capturing of the receptacle that matches the identification mark of each container to its order. This data and additional such as time, user ID, volume, etc. is transmitted to both the relevant monitoring unit and user. Upon completion of the urine collection, the receptacle containing the test tubes (or similar containers), is provided to clinic or the like to analyze the urine substances' variations. The substances analyze results together with the containers order that is already set, allows presenting graphs of variations in the urine content.

Figure 5:
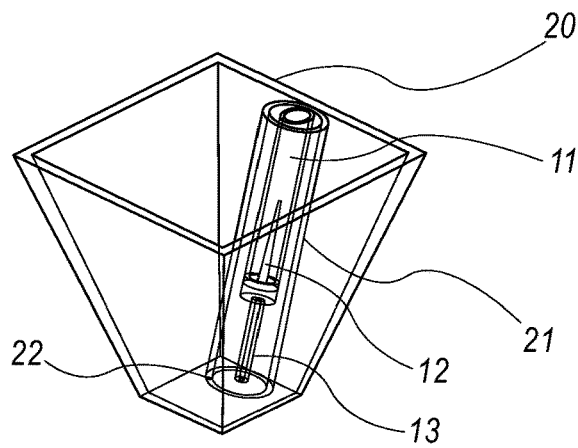
FIGS. 5 to 8 present respectively perspective view, top view, front view and side view of a second embodiment of a collector, according to certain features of the present invention.
Figure 6:
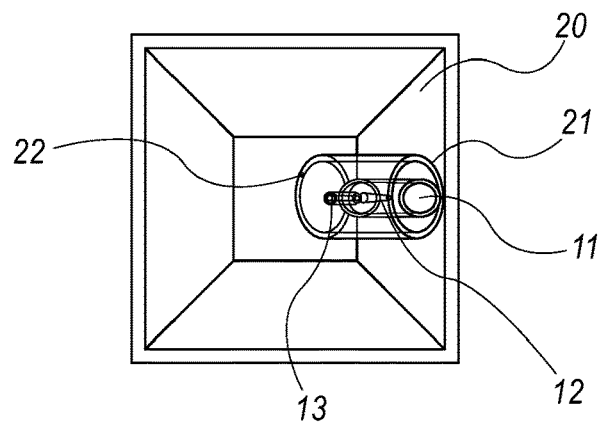
Figure 7:
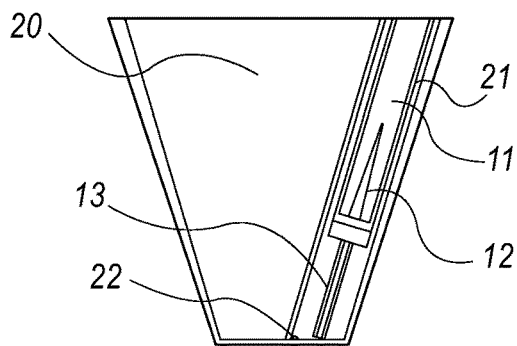
Figure 8:
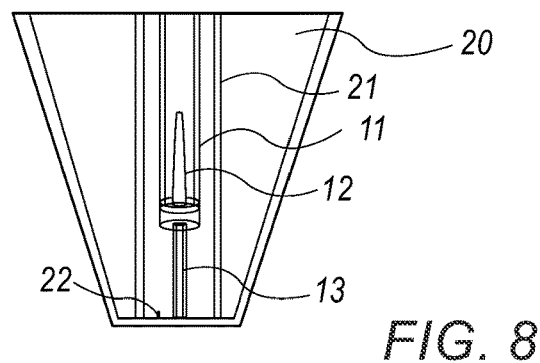
Figure 21:
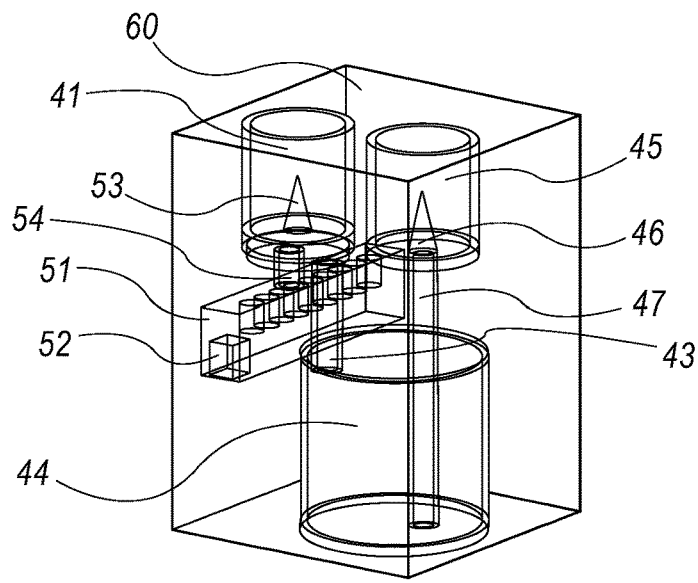
FIGS. 21 to 24 illustrate respectively a perspective view, top view, front view and side view of another embodiment of the receptacle, according to certain features of the present invention.
Figure 22:
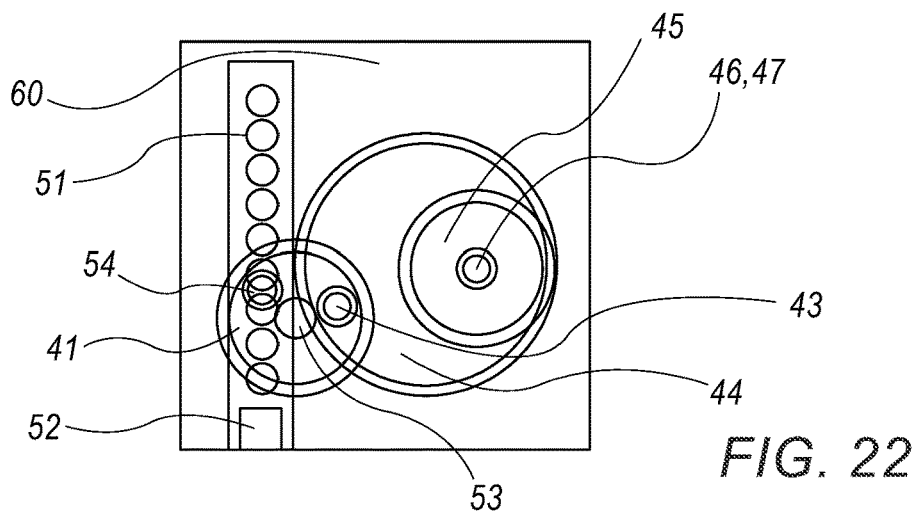
Figure 23:
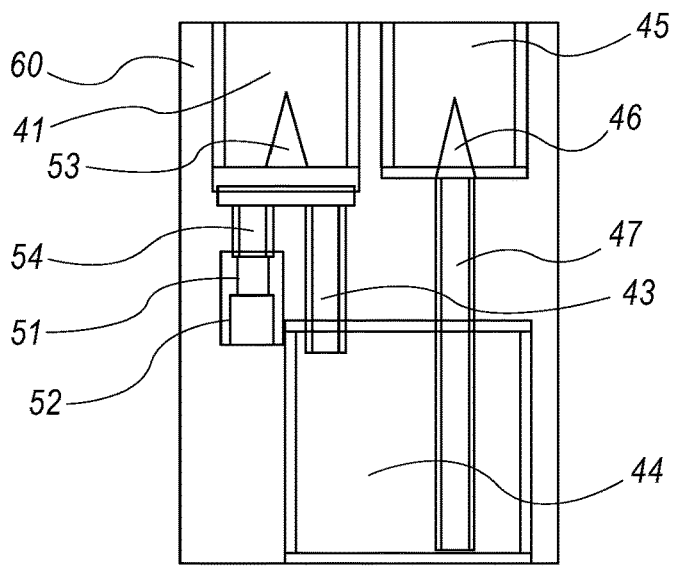
Figure 24:
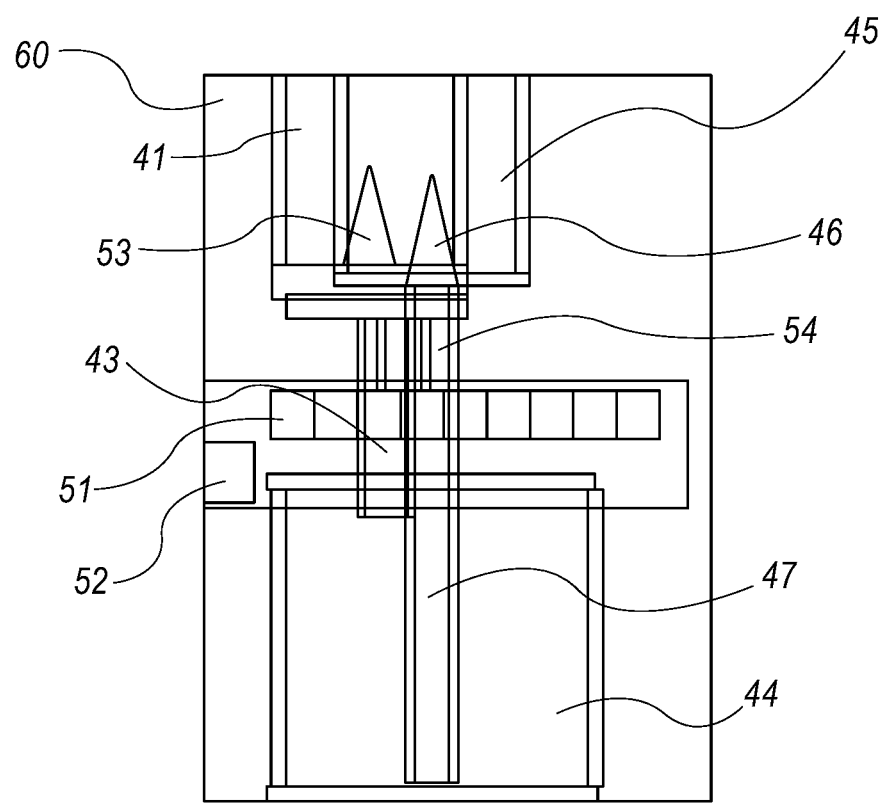
Figure 25:
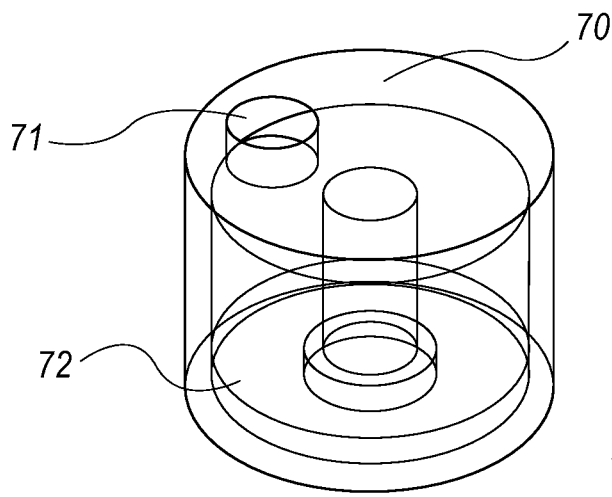
FIGS. 25 to 28 illustrate respectively a perspective view, top view, front view and side view of another embodiment of the receptacle, according to certain features of the present invention.
Figure 26:
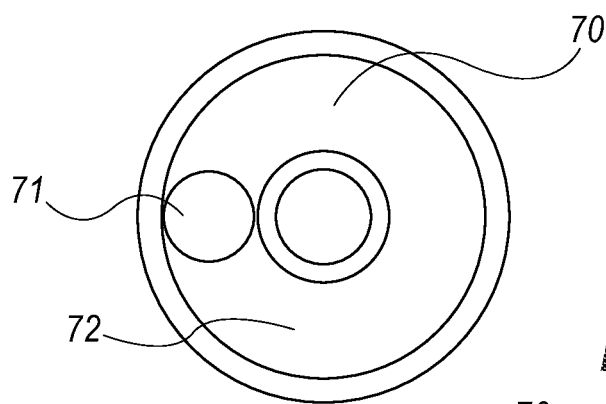
Figure 27:
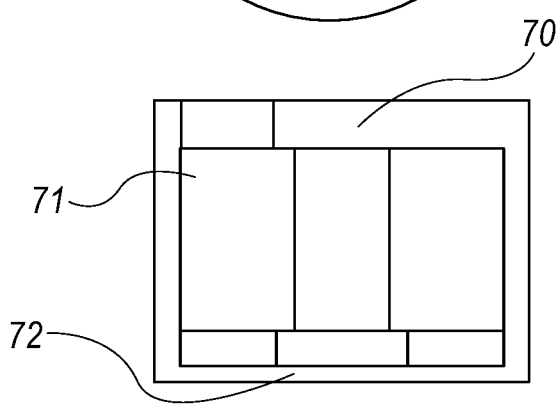
Figure 28:
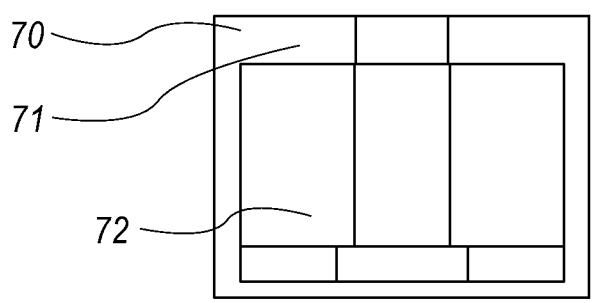

Embodiments of the collector as presented in FIG. 1, FIG. 5, and FIG. 9 may either be 'standalone', modular or combined into one. Embodiments of the receptacle as presented in FIG. 13 and FIG. 17 may be standalone, modular or combined as shown in FIG. 21, but not only. FIG. 25 depicts an additional type of a receptacle embodiment.

Figure 29:
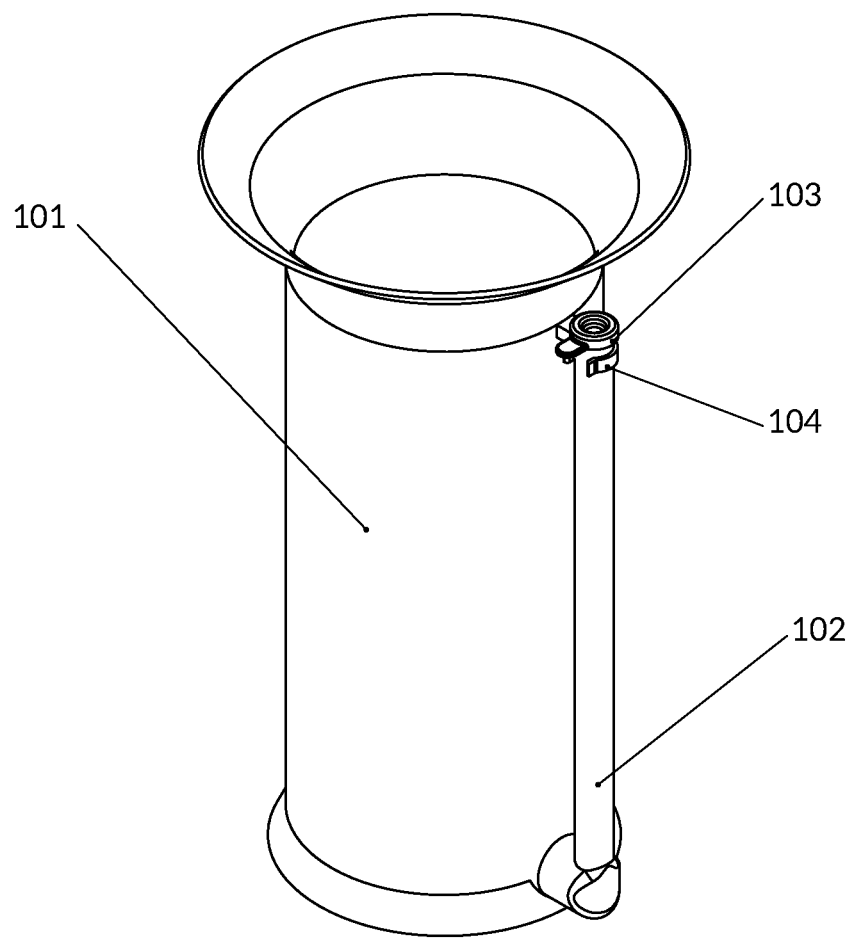
FIG. 29 to FIG. 31, each of which illustrates in an out-of-scale manner various views of a detachable container according to certain features of the present invention.
Figure 30:
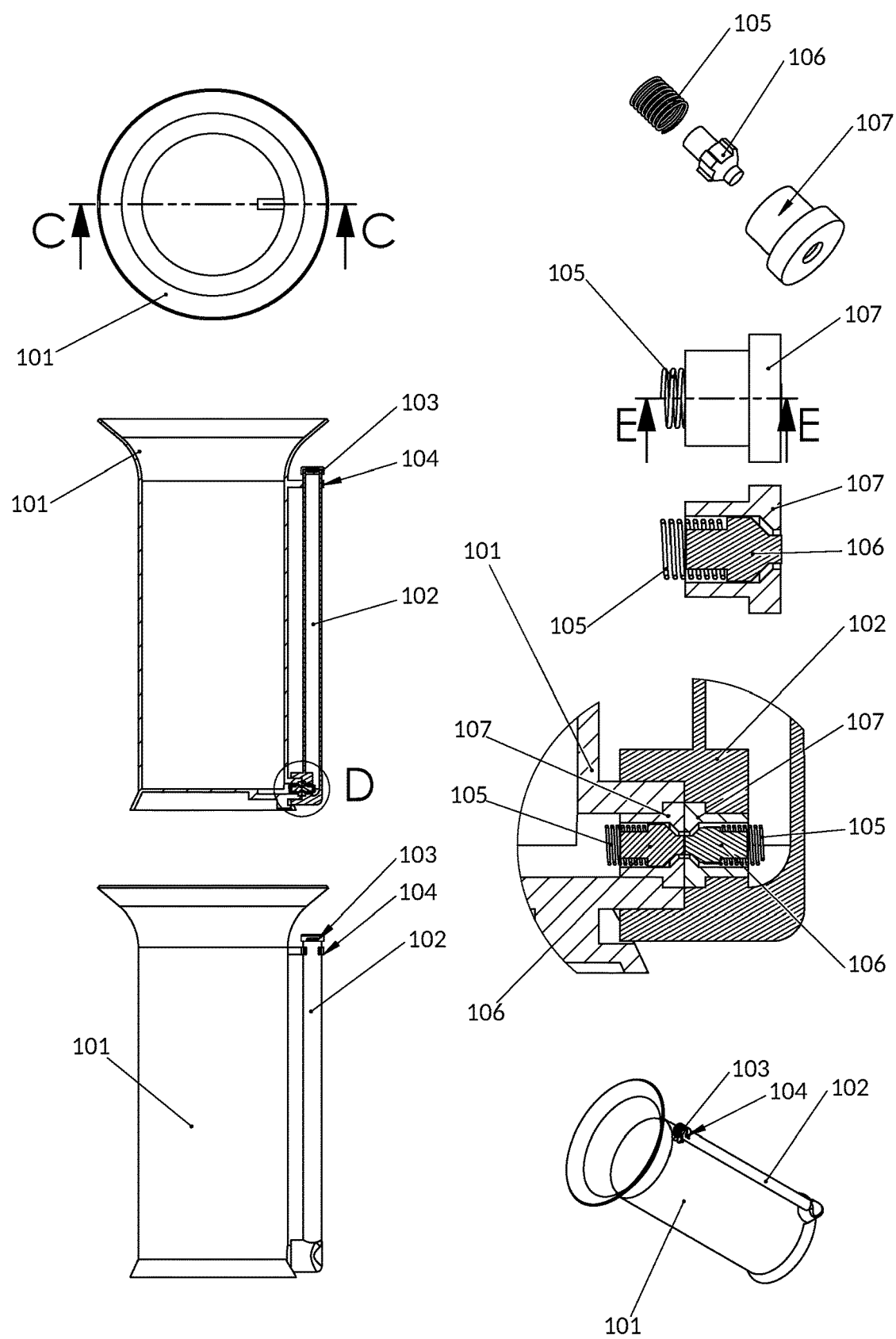
Figure 31:
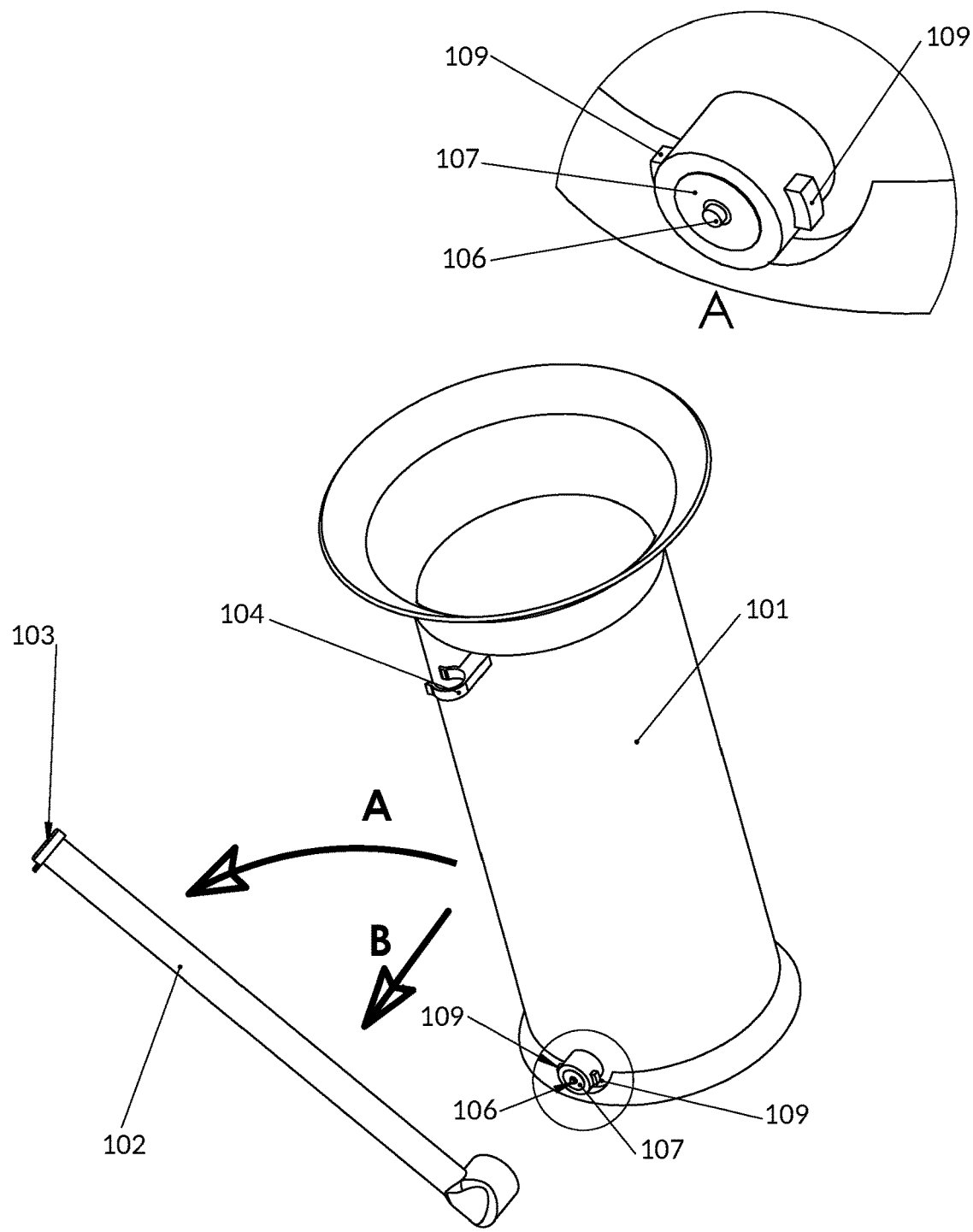

Reference is now made to FIG. 29 to FIG. 31 illustrating in an out-of-scale manner various views of a detachable sample tube (container or the like) of the invention. FIG. 29, illustrates a sample collector 101 and a sample tube 102 having an upper portion with a resealable opening 103, insertable or otherwise reversibly detachable (here, clip 104 and looking pins 109 depicted in FIG. 31) to the container. FIG. 30 illustrates a set of drawings of sample collector 101, sample tube 102 and various modules thereof. Drawing on the left and bellow; and on the right and bellow present a side view and a perspective view, respectively, of an apparatus of FIG. 29. On the left and at the middle, a lateral cross section (D) is shown, and left and upper figure show a cross section C:C of the same. Image on the right and above shows a perspective exploded view of the pumping mechanism, namely a housing (pushable handle 107), septum 106 and spring 105. A set of lateral views are shown on the right and below: including cross section E:E and fluid valve 106. FIG. 31 shows the same in a set of three perspective view, namely view A showing locking pins (or teeth, 109). Middle image shows connector 104 at top of the collector and the valves at the bottom. View below shows the detachable sample-tube taken out of its attachment (104) and fluid connection (106) by movements drawn as A and/or B. On the detachment of tube 102, the fluid in collector 101 might be emptied.

Figure 32:
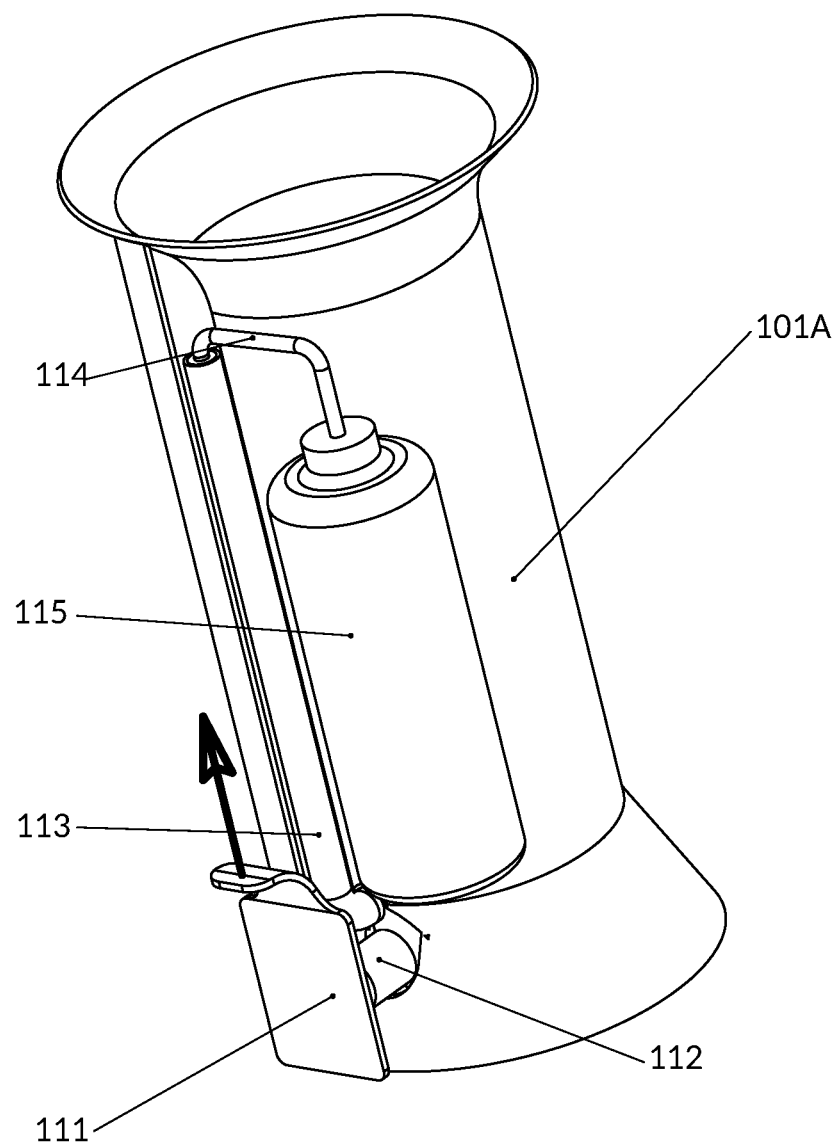
FIG. 32 to FIG. 33, each of which illustrates in an out-of-scale manner various views of a container and receptacle disposed on the vessel according to certain features of the present invention.
Figure 33:
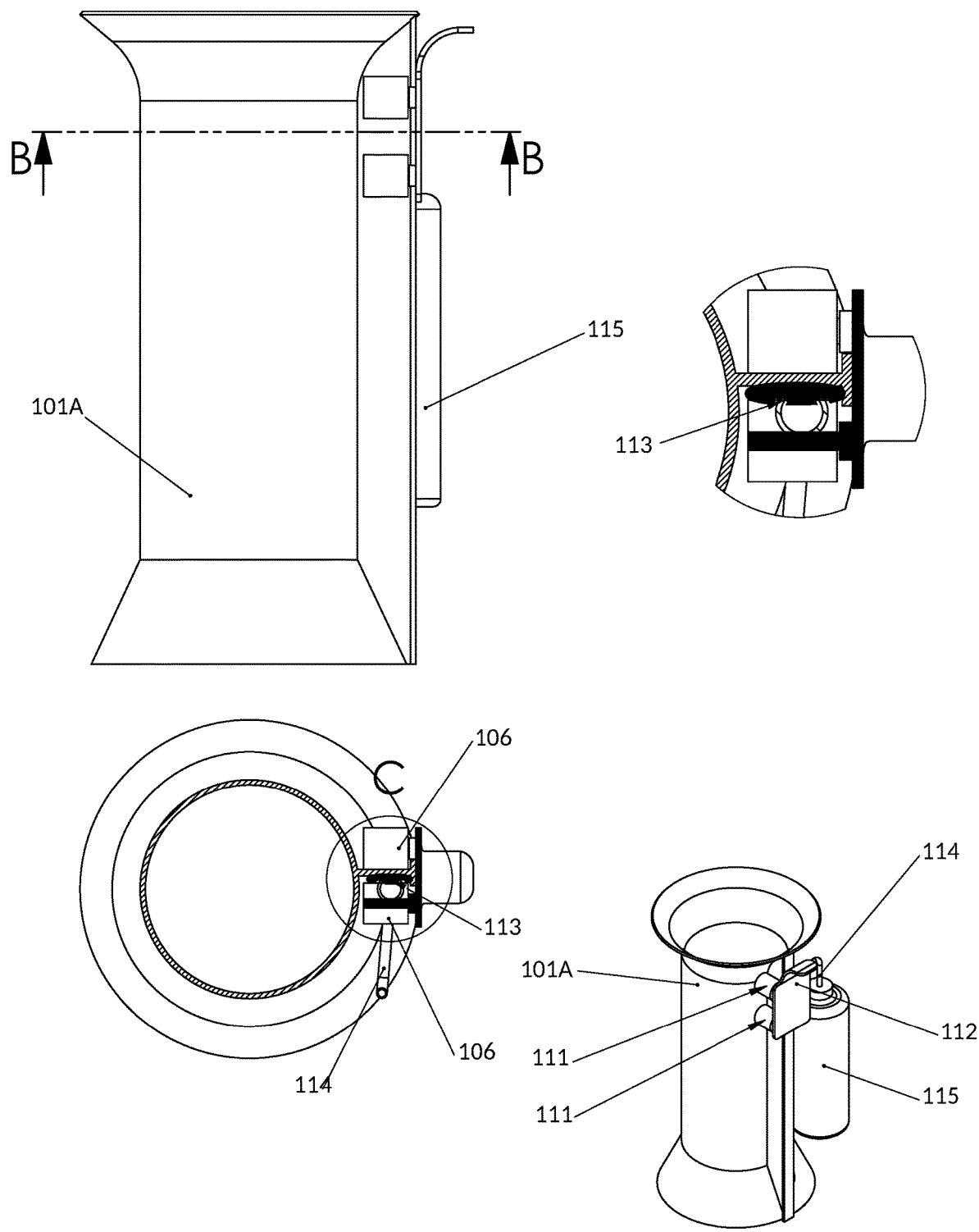

Reference is now made to FIG. 32, showing a perspective view of another embodiment of the technology, where collector 101A comprises a detachable receptacle 115 that is in fluid connection via (e.g., silicone) piping 114 with tube-like vessel 113. It is well in the scope of the invention that a volume of fluid, collected in the sample tube, is directed to a receptacle which is attached to the collector. The aforesaid collection is provided either (i) each time, namely after every session of urination, or (ii) constantly, hence enabling an accumulate collection of all urine given along all sessions of urination along a predefined long period of time. The fluid flowing mechanism is, e.g., an either manually operated or mechanically activated roller 112 having a plurality of rolls, all are attached to handle 111. Mechanically activated mechanism is selected e.g., from electrical engine, spring loaded mechanism, screw-type mechanism, etc. FIG. 33, shows a set of images presenting the same: a perspective view on the bottom right, top detailed view on the bottom left and top right portion (section B:B), and side view (see there section B:B).

Figure 34:
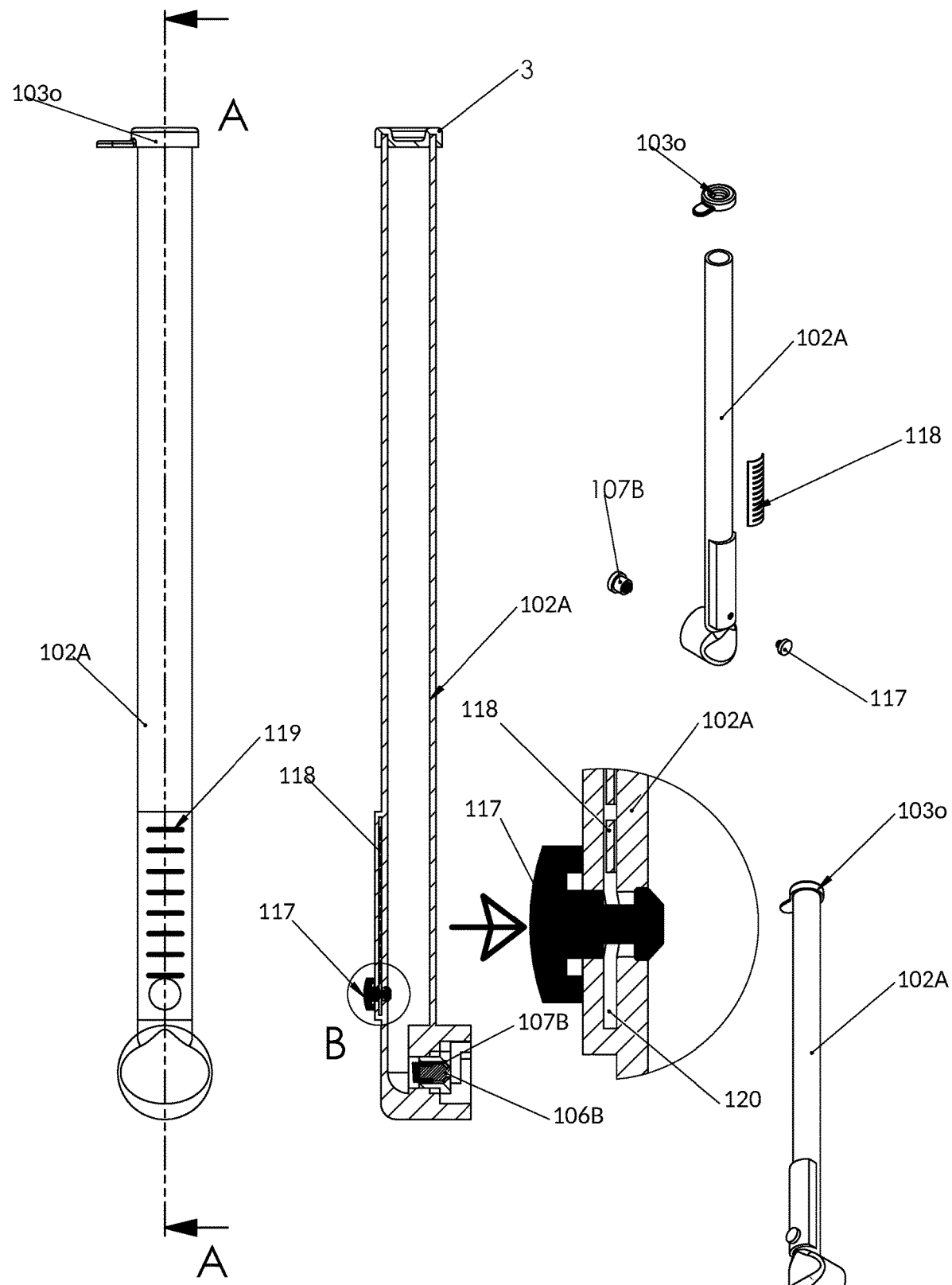
FIG. 34 illustrates in an out-of-scale manner various views of a container disposed with a sensor according to certain features of the present invention.

Reference is now made to FIG. 34, depicting a series of side views (some are cross sections) of a sample tube-like vessel 102A provided in connection with one or more sensors and/or diagnostic means, here is shown a commercially available urine dipstick 118. The sample tube comprises a top sealable opening 103o, sleeve-like elongated vessel of a predefined volume (102A). It is well in the scope of the invention wherein said dipstick 118 is provided either or both (i) inside the sample tube, or (ii) outside the tube, as shown here. Dipstick 118 is reversibly or permanently accommodated within a drawer 119. Pushable pin 117 enables a puncturing short-movement, see arrow at zoomed view B, for wetting of the surface of the dipstick by urine located at volume 120 so analysis is enabled by the surface.

Figure 35:
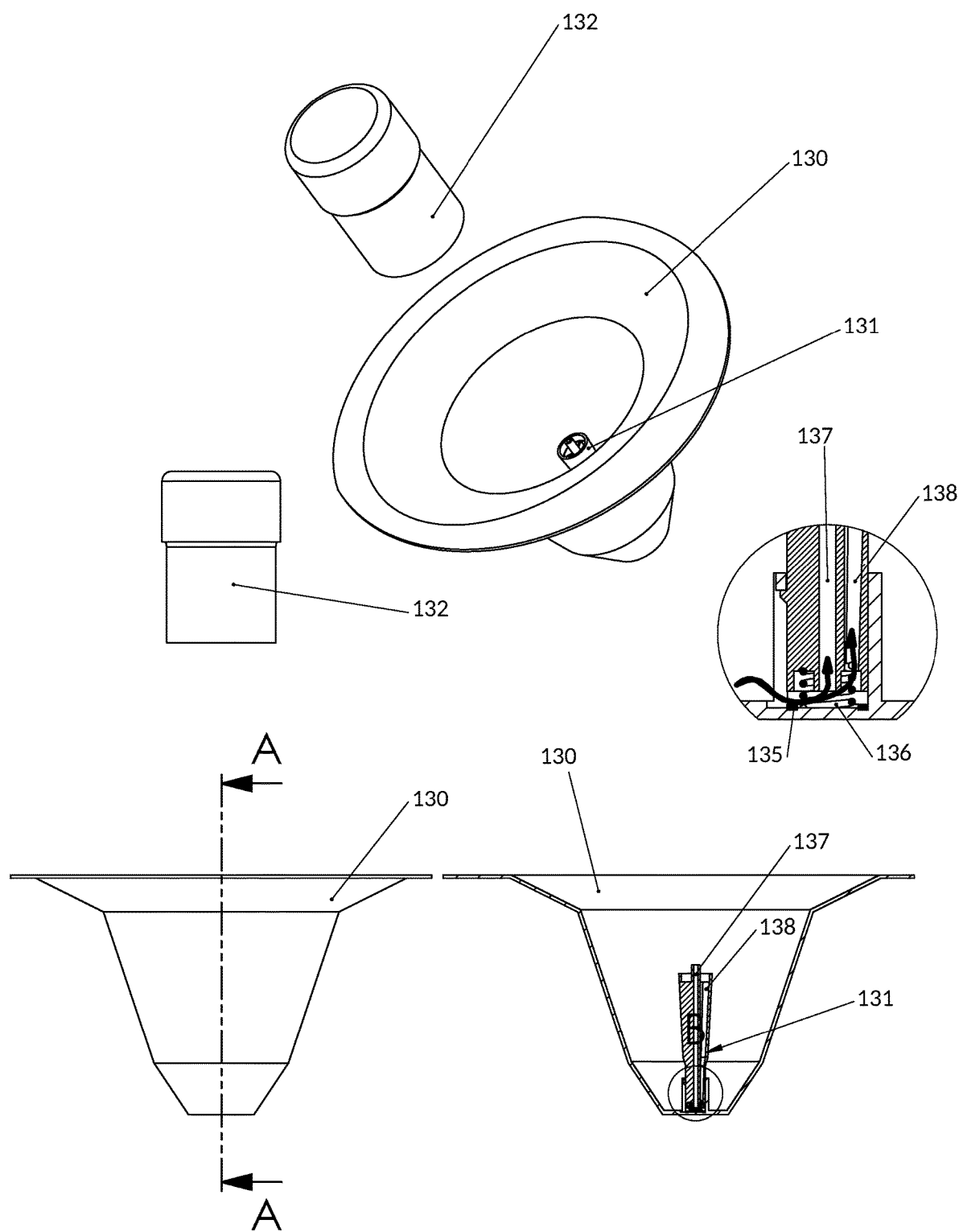
FIG. 35 to FIG. 38, each of which illustrates in an out-of-scale manner various views of a vessel disposed with a sleeve-like container and a combined sample collector and a receptacle according to certain features of the present invention.

Reference is now made to FIG. 35 presenting a set of figures of a mechanism to sample urine from collector 30 to an external container, according to yet another embodiment of the invention. Pump head 132 is activatable by pushing along axis A:A, tangent to collector's 130 main plain. Pump 131 exceeds along axis A:A is configured by means of size and shape to accept the plunger. A zoomed view of part B is presented in the mid right side, showing a cross section of the pump, comprising urine collecting conduit 137 of a predefined volume 131. The urine flow is hence facilitated by pump-wise pressuring air-column 138 and utilizing air piping 135, from the collector topmost portion 130 to conduit 137, and by connecting those vessels, to volume 131 in order to feed an external container, such as pump head 132.

Figure 36:
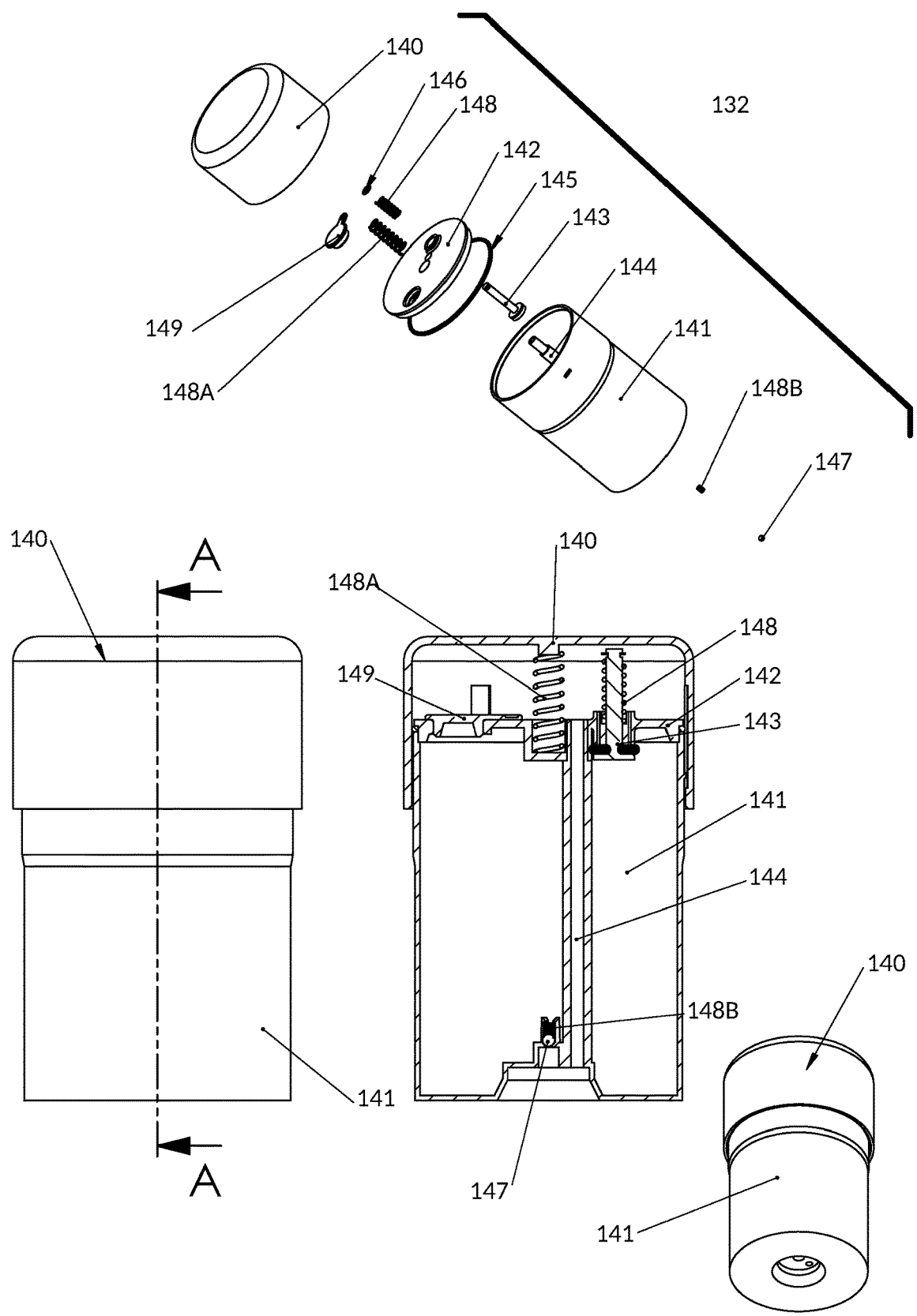
Figure 37:
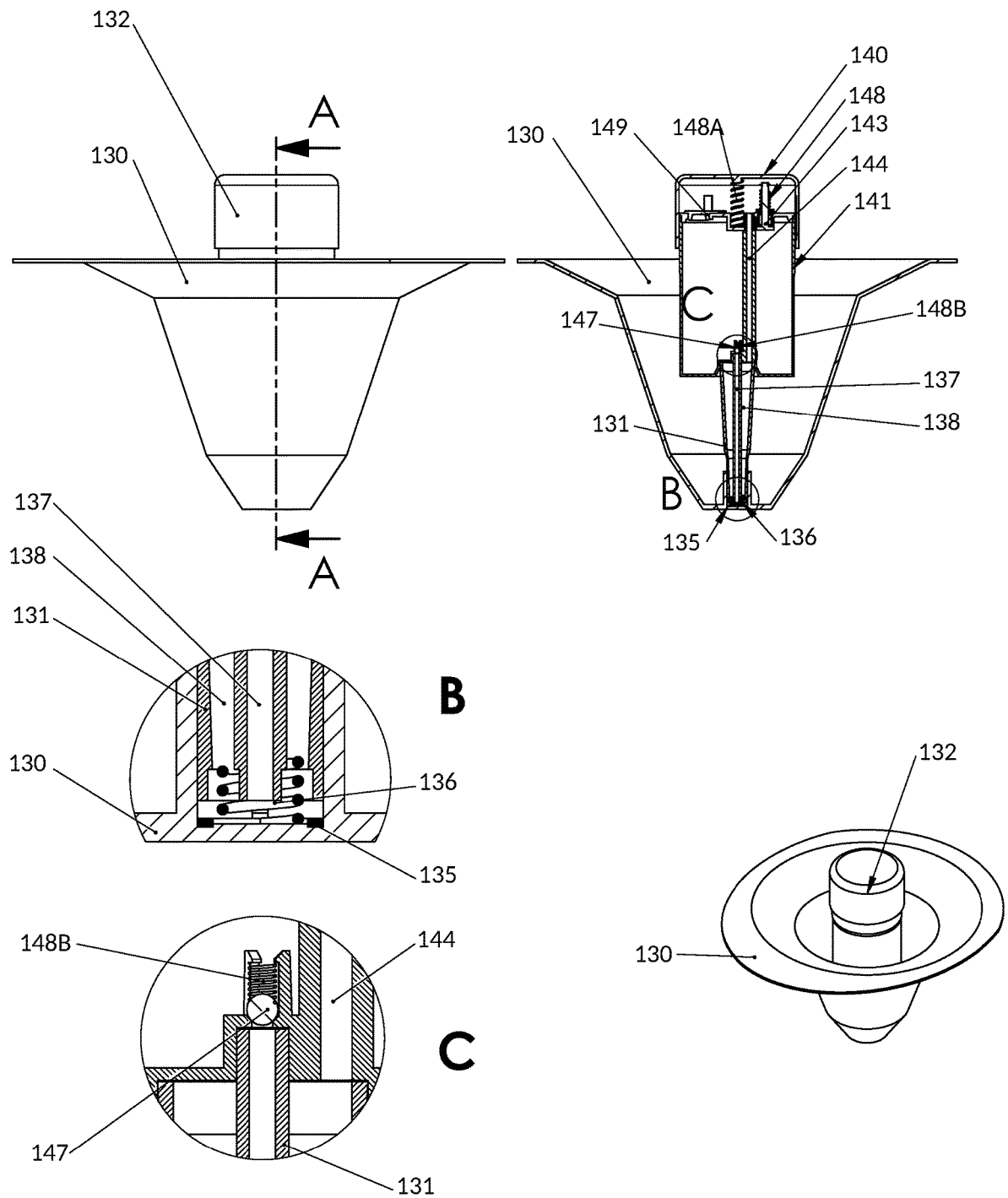
Figure 38:
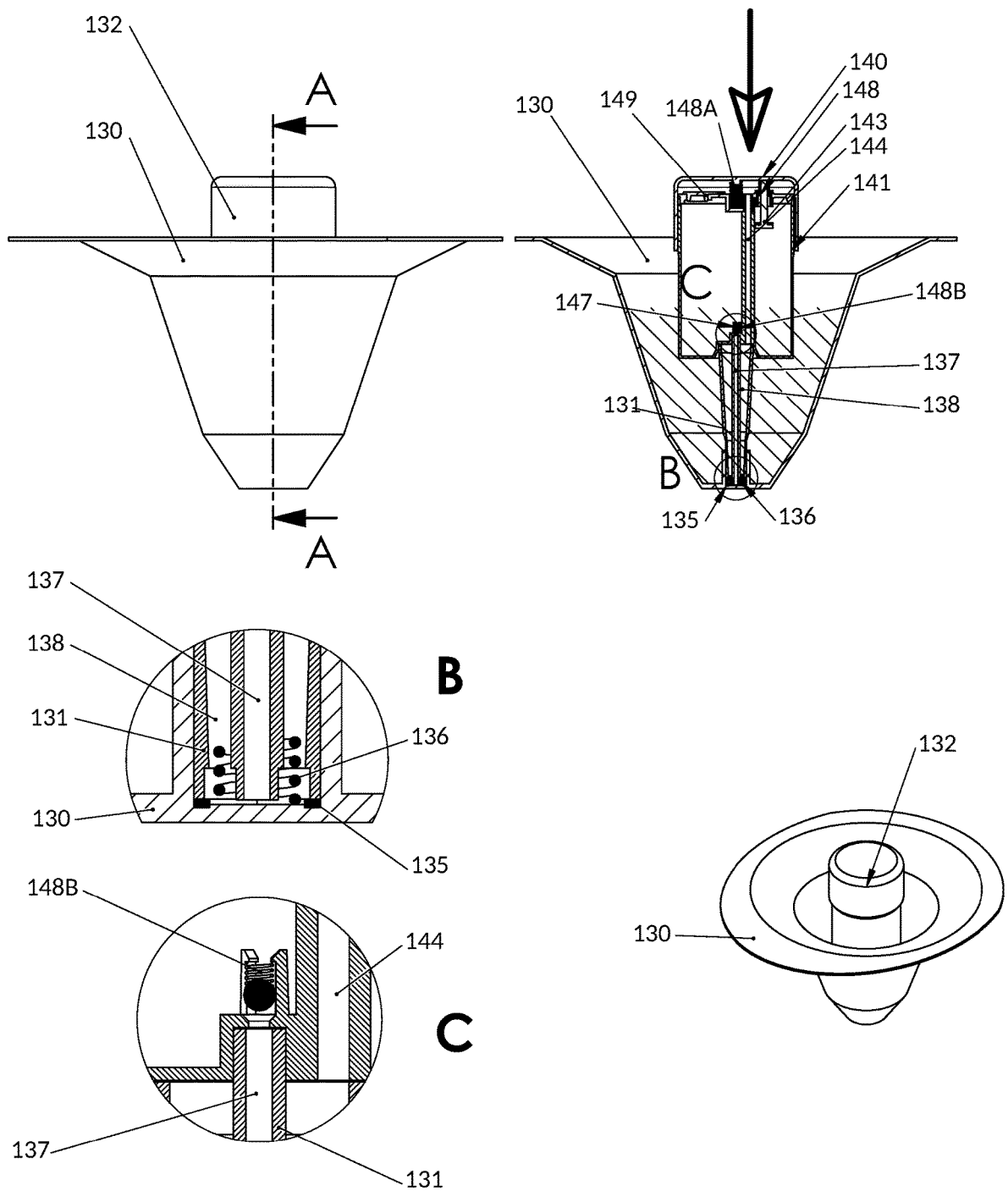

Reference is now made to FIGS. 36 to 38 presenting a set of figures of yet another embodiment of the invention. Plunger 140 is activatable by pushing along axis A:A.

Plunger proximal end is pushed by user's hand. Plunger's distal portion envelopes housing 141. An exploded view of the pump mechanism (partially located in pump head 132) is depicted in the upper image: press button 140 provides for an efficient air pressure; O-ring 146, cup 149 and two springs 148 and 148A are illustrated on the right portion of plunger 142 having a distal O-ring 145 and a screw-like member of possibly alterable effective-length 143, inner volume 144 and compressed air-volume. At the proximal portion of the image, spring 148B and fluid-valve are shown. FIG. 37 details the same in a first step, where plunger is nit ye compressed, and FIG. 38 depicts the same in the hereto operated mode of action.

Figure 39:
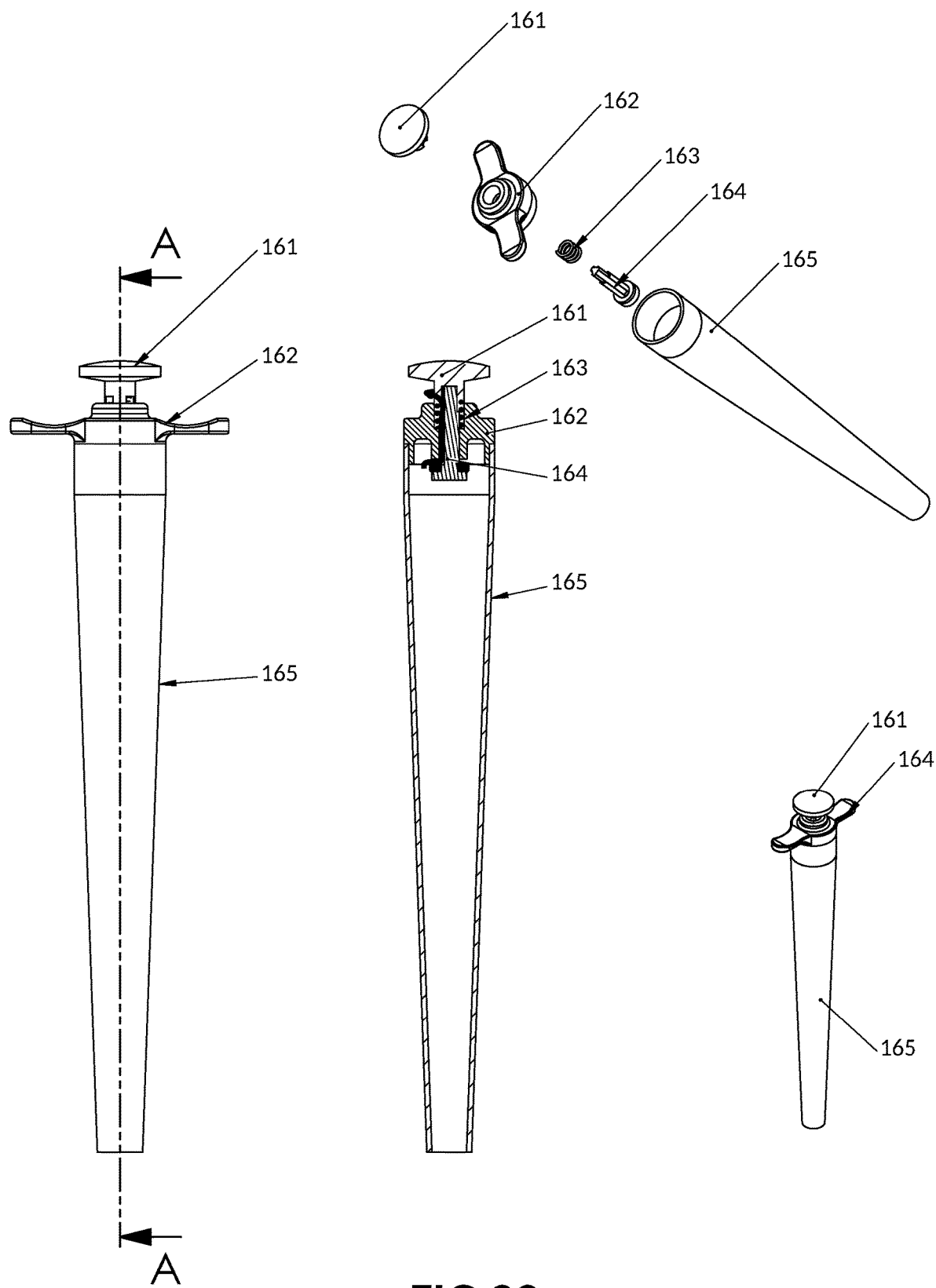
FIG. 39 illustrates in an out-of-scale manner various views of another sub-pressure sample container according to certain features of the present invention.
Figure 40:
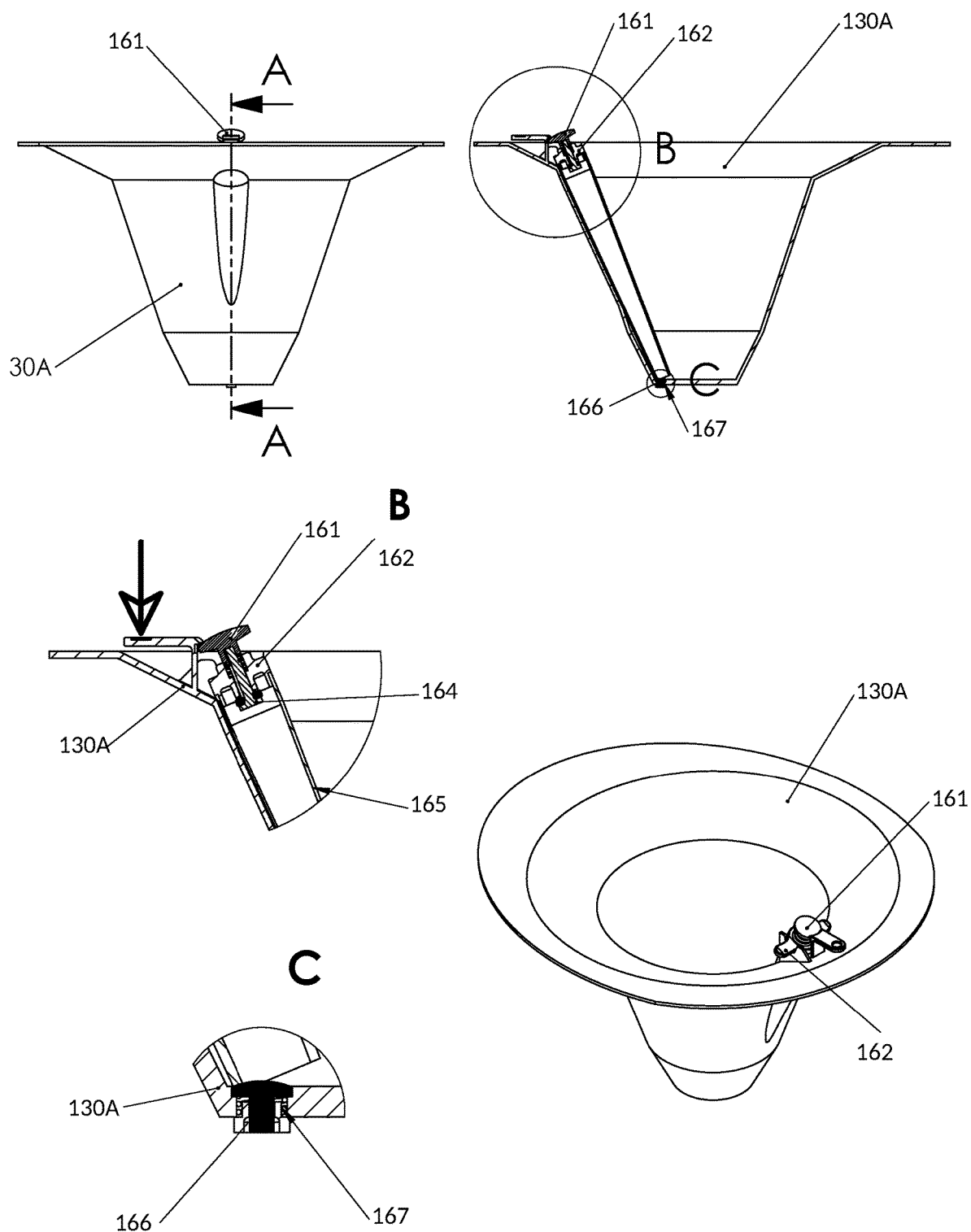
FIG. 40 and FIG. 41, each of which illustrates in an out-of-scale manner various views of a combined sample collector and a receptacle according to certain features of the present invention.
Figure 41:
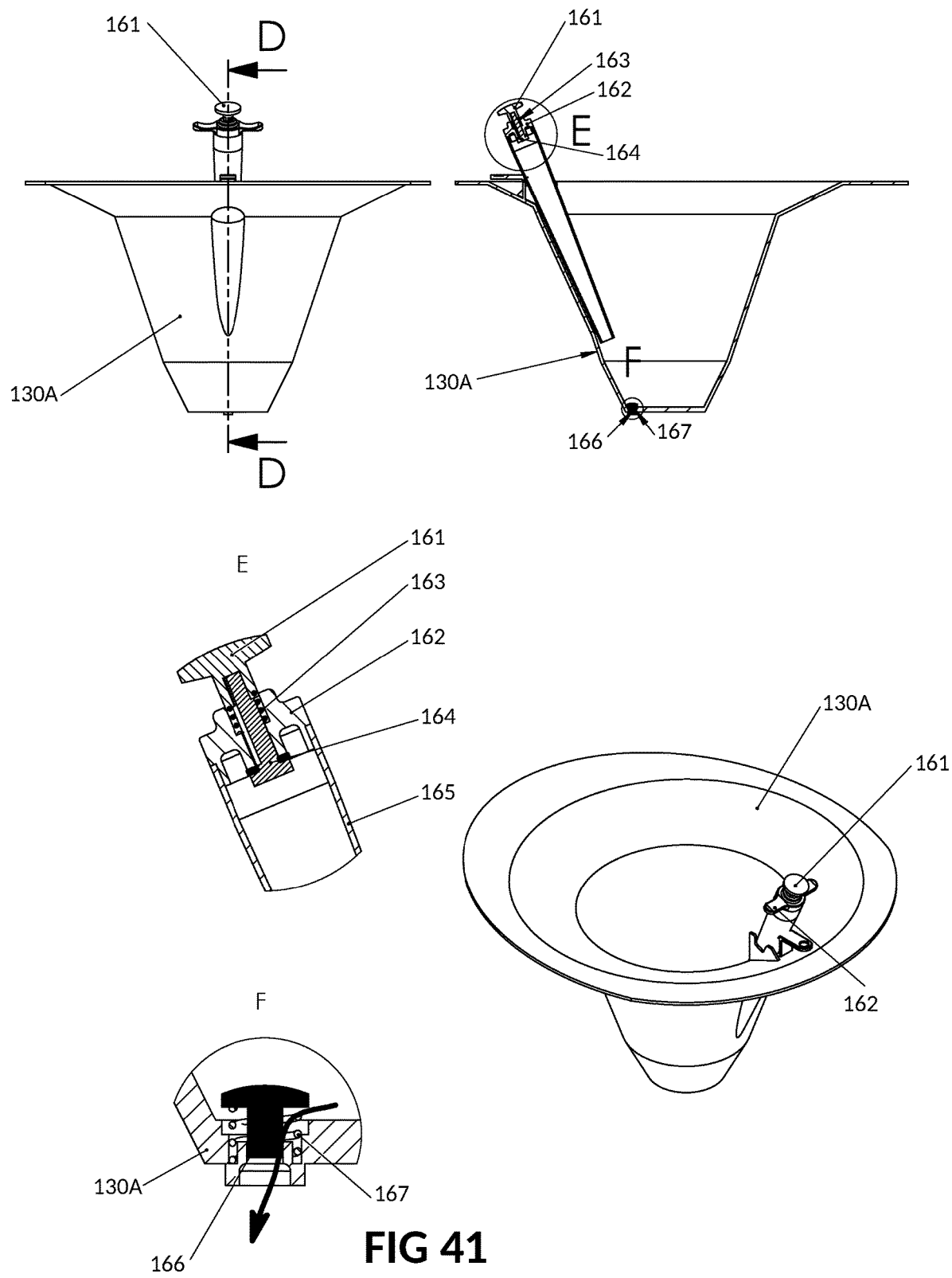

Reference is now made to FIGS. 39 to 41, all are illustrating a set of figures of yet another embodiment of a sub-pressure sample container. Pump head 161 is activatable by pushing along axis A:A, being the main longitudinal axis of the elongated vessel 165. This mechanism enables user to facilitate fluid's flow by concurrently pressing thumb rest 161 and flange 162. Pump mechanism is provided in the proximal portion of sample tube 165. Mechanism comprises the thumb rest 161 and flange 162, spring 163, valve 164 and sample tube 165. FIG. 40 shows that same, where sample tube 165 is reversibly attached, in an eccentric manner, inside collector's urine receiving cone 130A. Said attachment is possibly enables by utilizing lever, springs as depicted in view C, see members 130A, 166 and 164. FIG. 41 shows that same, where the sample tube is not yet fully inserted to its place adjacent to the inner surface of the collector's extension lip (cone 130A).

Figure 42:
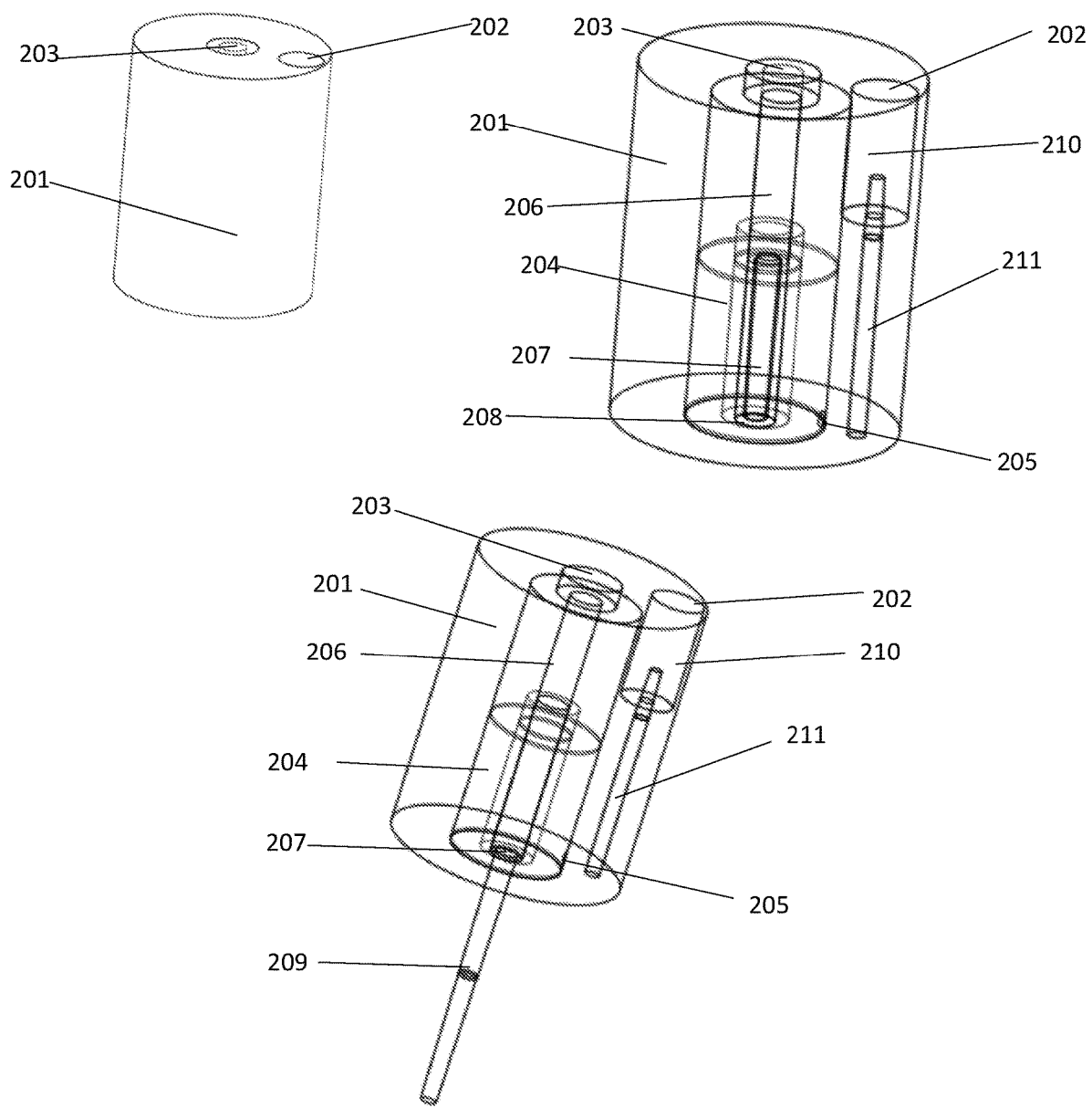
FIGS. 42 to 44, each of which illustrates in an out-of-scale manner various views of yet another combined sample collector and a receptacle according to certain features of the present invention.
Figure 43:
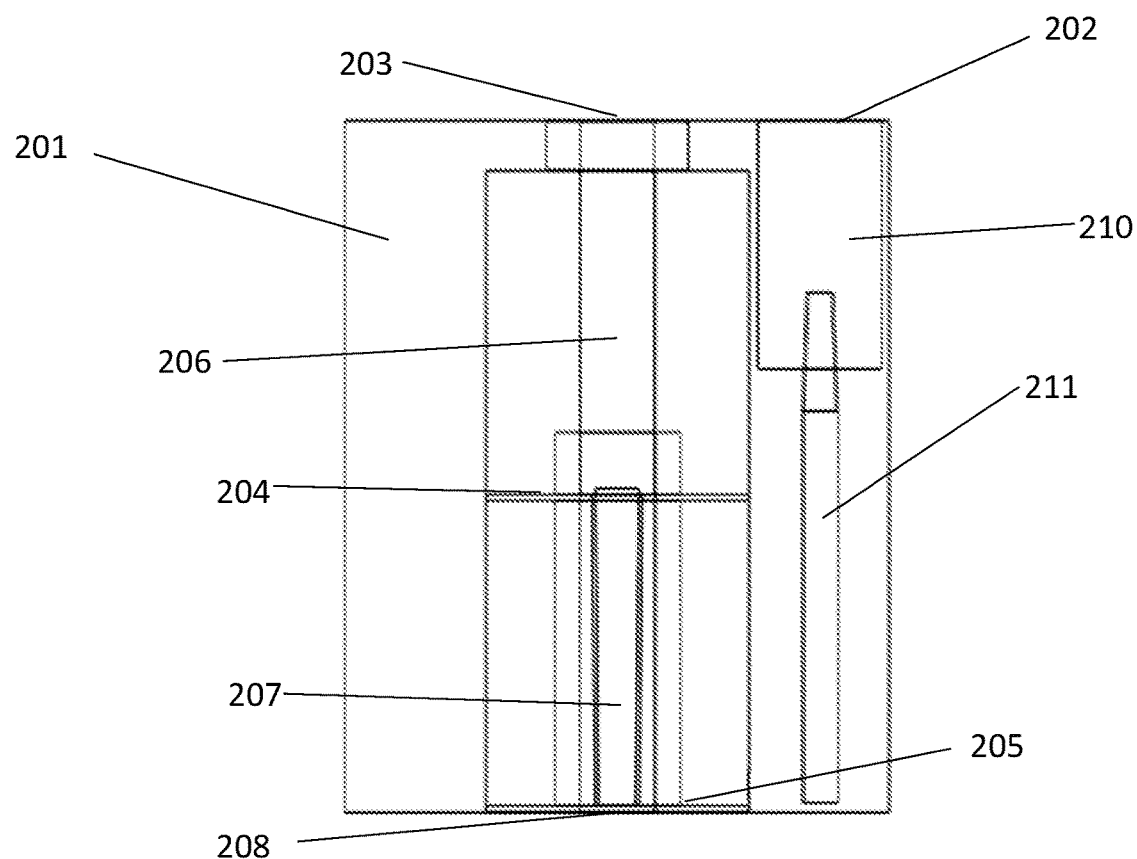
Figure 44:
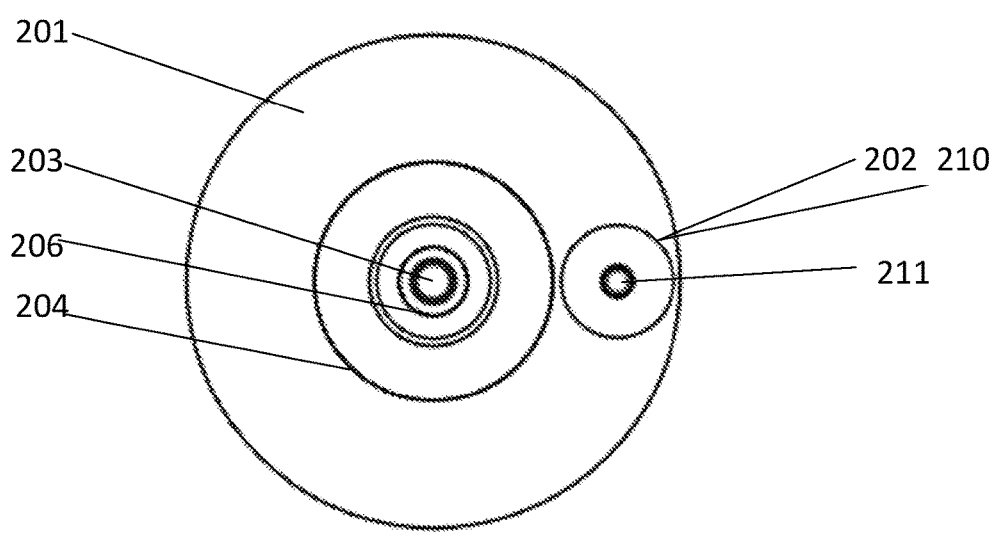

Reference is finally made to FIGS. 42 to 44, all are illustrating various views of yet another embodiment of the invention, namely a combined sample collector and a receptacle to absorb all samples. As schematically shown here, sample collector and absorber (receptacle 201) reversibly or temporarily accommodates a tube insert 202 configured to obtain the final sample. Also shown is a button to manual or powered activation of chain actions at each urine sample collection: Pushing down the syringe feeding pipe and extension pipe through a closed end of the syringe. Pulling up the syringe piston to take in the urine sample. Pushing down the syringe piston to let the urine sample flow through a one-way valve, to the receptacle part of the device, where all samples are absorbed. Closing the open end of the syringe. The feeding and extension pipes could either be a part of the device or separately mounted prior to the button activation. The mechanism comprises a syringe 204; an opening with a one-way valve 205; room for the chain activities mechanism, either electrically powered or mechanical through springs or similar 206; syringe feeding pipe and extension pipe stored in the device 207; syringe one-way valve or seal 208; syringe feeding pipe and extension pipe 209; Tube pocket (insert) 210; and Feeding pipe (for final sample) 211.

The present disclosure is to be considered as an exemplification of the disclosure and is not intended to limit the disclosure to the specific embodiments illustrated by the figures or description below.

While the invention has been described with respect to a limited number of embodiments, it will be appreciated that many variations, modifications and other applications of the invention may be made.

The invention claimed is:

1. A system comprising:
   a collector, wherein the collector is configured to fit on top, or at least partially inside a toilet; and
   a mechanism configured to: repeatedly collect urine samples inside said collector and extract volumes of urine a plurality of instances during a previously determined time period;
   a receptacle; wherein for all said instances, a volume of urine is transferable to the receptacle, wherein urine accumulated in the receptacle is proportional to a total volume of urine collected in said collector during the previously determined time period with a known proportionality constant.

2. The system according to claim 1, wherein the collector includes a pocket configured to receive a sealed container with a seal; wherein said sealed container is insertable into the pocket to penetrate said seal by said pocket.

3. The system according to claim 1, wherein said collector comprises a first compartment and a second compartment; and a mechanism configured to separate a first urine volume provided by an initial urine flow, into the first compartment, from a second urine volume provided from a subsequent urine flow, into the second compartment, wherein only said second urine volume of the second compartment is extracted.

4. The system according to claim 1, further comprising a hollow sleeve disposed either inside or outside the collector; wherein urine disposed inside said collector and inside said sleeve attain the same fluid level responsive to a fluid passage between said collector and said sleeve at the bottom of the collector, the system further comprising:
   a mechanism configured for closing fluid passage between said collector and said sleeve when said sample of urine is extracted.

5. The system according to claim 1, further comprising:
   a sensor configured to measure a parameter of the urine accumulated in the receptacle, wherein said receptacle is characterized by a transparent face so that an image of either said urine or said sensor is captured through said transparent face of said receptacle.

6. A method for collecting urine, comprising:
   providing a collector;
   placing said collector on top or at least partially inside a toilet ;
   upon collecting urine inside the collector, extracting a sample of urine from inside said collector;
   repeatedly collecting urine samples and extracting volumes of urine a plurality of instances during a previously determined time period;
   for all said instances, transferring a volume of urine contained to a receptacle, wherein urine accumulated in the receptacle is proportional to a total volume of urine collected in said collector during the previously determined time period with the known proportionality constant.

7. The method according to claim 6, wherein the collector includes a pocket configured to receive a sealed container with a seal, the method further comprising:
   inserting said sealed container into the pocket thereby penetrating said seal by the pocket prior to said extracting the sample of urine into said sealed container.

8. The method according to claim 6, further comprising:
   providing said collector with a plurality of compartments;
   separating an initial urine flow from a subsequent urine flow; and
   said extracting said sample of urine only from a compartment including said subsequent urine flow.

9. The method according to claim 6, wherein said collector includes a hollow sleeve disposed inside or outside said collector, wherein urine disposed inside said collector and inside said sleeve attain the same fluid level responsive to a fluid passage between said collector and said sleeve at the bottom of said collector, the method further comprising:
upon said collecting of said urine sample, closing a fluid passage between said collector and said sleeve.

10. The method according to claim 6, further comprising:
providing a sensor configured to measure a parameter of the urine accumulated in the receptacle, wherein said receptacle is characterized by a transparent face so that an image of either said urine or said sensor is captured through said transparent face of said receptacle.

11. A urine collection and sampling vessel comprising:
a collector configured for collecting urine;
a detachable container disposed either inside or outside the collector, with fluid passage to the collector; and
a mechanism configured to close the fluid passage between the collector and the container and when the detachable container is detached, provide a sample of urine inside the detachable container, wherein urine disposed inside the collector and inside the detachable container attain the same fluid level responsive to the fluid passage between the collector and the container at the bottom of the collector.

12. The vessel according to claim 11, further comprising:
a receptacle, wherein a plurality of urine samples disposed in the detachable container are transferable to the receptacle; wherein urine accumulated in said receptacle is proportional to a total volume of urine collected during a previously determined time period with a known proportionality constant.

13. The vessel according to claim 11, further comprising a sensor configured to measure a parameter of the urine accumulated in the vessel.

14. A method for collecting urine, the method comprising:
providing a collector assembled with a detachable container disposed either inside or outside the collector with fluid passage to the collector;
placing said collector on top or at least partially inside a toilet;
attaining same fluid level responsive to a fluid passage between the collector and the container; and
upon detaching the detachable container, closing the fluid passage between the collector and the container and providing a sample of urine inside the detachable container.

* * * * *